(12) United States Patent
Tanabe et al.

(10) Patent No.: US 10,371,631 B2
(45) Date of Patent: Aug. 6, 2019

(54) OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

(71) Applicant: OLYMPUS CORPORATION, Tokyo (JP)

(72) Inventors: Tetsuya Tanabe, Tokyo (JP); Mitsushiro Yamaguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 595 days.

(21) Appl. No.: 14/188,375

(22) Filed: Feb. 24, 2014

(65) Prior Publication Data

US 2014/0170760 A1    Jun. 19, 2014

Related U.S. Application Data

(63) Continuation of application No. PCT/JP2012/068947, filed on Jul. 26, 2012.

(30) Foreign Application Priority Data

Aug. 26, 2011  (JP) .................................. 2011-184634

(51) Int. Cl.
*G01N 21/64* (2006.01)
*G02B 21/00* (2006.01)

(52) U.S. Cl.
CPC ............ *G01N 21/64* (2013.01); *G01N 21/645* (2013.01); *G01N 21/6408* (2013.01);
(Continued)

(58) Field of Classification Search
CPC ............... G01N 21/64; G01N 21/6408; G01N 21/6458; G01N 21/6486; G01N 21/6452;
(Continued)

(56) References Cited

U.S. PATENT DOCUMENTS 4,251,733 A    2/1981 Hirleman, Jr.
4,885,473 A    12/1989 Shofner et al.
(Continued)

FOREIGN PATENT DOCUMENTS

CN    101946180 A     1/2011
EP    1 906 172 A1    4/2008
(Continued)

OTHER PUBLICATIONS

Chinese Office Action dated Oct. 10, 2014, issued in Chinese Application No. 201280005999.8; w/English Translation. (20 pages).
(Continued)

*Primary Examiner* — Rebecca M Fritchman
(74) *Attorney, Agent, or Firm* — Westerman, Hattori, Daniels & Adrian, LLP

(57) ABSTRACT

There is provided an optical analysis technique of detecting light of a light-emitting particle in a sample solution in the scanning molecule counting method using the light measurement with a confocal or multiphoton microscope, for suppressing the scattering in detected results of signals of light of light-emitting particles smaller and achieving the improvement of accuracy. The inventive technique comprises moving the position of a light detection region along a predetermined route for multiple circulation times by changing the optical path of the optical system; detecting light from the light detection region and generating time series light intensity data during the moving of the light detection region and detecting individually a signal indicating light from each light-emitting particle existing in the predetermined route using the time series light intensity data obtained in the circulating movements of the light detection region of multiple times.

18 Claims, 8 Drawing Sheets

(52) U.S. Cl.
CPC ..... *G01N 21/6452* (2013.01); *G01N 21/6458* (2013.01); *G01N 21/6486* (2013.01); *G02B 21/0032* (2013.01); *G02B 21/0048* (2013.01); *G02B 21/0076* (2013.01); *Y10T 436/143333* (2015.01)

(58) Field of Classification Search
CPC ...... Y10T 436/143333; G02B 21/0076; G02B 21/0032; G02B 21/0048
USPC ............ 436/94, 172; 250/459.1, 206, 458.1; 422/52, 82.08
See application file for complete search history.

(56) References Cited

U.S. PATENT DOCUMENTS

| | | | |
|---|---|---|---|
| 4,979,824 | A | 12/1990 | Mathies et al. |
| 5,319,575 | A * | 6/1994 | Lilienfeld ............... G01N 21/53 702/26 |
| 5,866,336 | A | 2/1999 | Nazarenko et al. |
| 5,900,933 | A | 5/1999 | Schwartz et al. |
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,449,042 | B1 | 9/2002 | Hamann |
| 6,563,583 | B2 | 5/2003 | Ortyn et al. |
| 6,710,871 | B1 | 3/2004 | Goix |
| 6,782,297 | B2 | 8/2004 | Tabor |
| 6,856,391 | B2 | 2/2005 | Garab et al. |
| 6,927,401 | B1 | 8/2005 | Palo |
| 8,284,484 | B2 | 10/2012 | Hoult et al. |
| 9,068,944 | B2 | 6/2015 | Tanabe |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2003/0036855 | A1 | 2/2003 | Harris et al. |
| 2003/0218746 | A1 | 11/2003 | Sampas |
| 2004/0022684 | A1 | 2/2004 | Heinze et al. |
| 2004/0036870 | A1 | 2/2004 | Goix |
| 2004/0051051 | A1 | 3/2004 | Kato et al. |
| 2004/0150880 | A1 | 8/2004 | Nakata et al. |
| 2005/0260660 | A1 | 11/2005 | van Dongen et al. |
| 2006/0078998 | A1 | 4/2006 | Puskas et al. |
| 2006/0158721 | A1 | 7/2006 | Nakata et al. |
| 2006/0256338 | A1 | 11/2006 | Gratton et al. |
| 2007/0250274 | A1 | 10/2007 | Volkov et al. |
| 2008/0052009 | A1 | 2/2008 | Chiu et al. |
| 2008/0156999 | A1 | 7/2008 | Nishiwaki et al. |
| 2008/0158561 | A1 | 7/2008 | Vacca et al. |
| 2009/0159812 | A1 * | 6/2009 | Livingston ............ B01L 3/5085 250/428 |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2010/0301231 | A1 | 12/2010 | Yamaguchi |
| 2011/0001969 | A1 * | 1/2011 | Ishii ...................... G01J 3/4412 356/337 |
| 2011/0192595 | A1 | 8/2011 | Ronaes et al. |
| 2013/0122488 | A1 | 5/2013 | Tanabe et al. |
| 2013/0228705 | A1 | 9/2013 | Nishikawa et al. |
| 2013/0228706 | A1 | 9/2013 | Yamaguchi et al. |
| 2013/0242307 | A1 | 9/2013 | Hanashi et al. |
| 2014/0099630 | A1 | 4/2014 | Nakata |
| 2014/0134608 | A1 | 5/2014 | Hanashi et al. |
| 2014/0162268 | A1 | 6/2014 | Tanabe et al. |

FOREIGN PATENT DOCUMENTS

| | | |
|---|---|---|
| EP | 2 752 655 A | 7/2014 |
| EP | 2 840 380 A1 | 2/2015 |
| JP | 63-225145 A | 9/1988 |
| JP | 4-337446 A | 11/1992 |
| JP | 2002-507762 A | 3/2002 |
| JP | 2002-543414 A | 12/2002 |
| JP | 2004-506192 A | 2/2004 |
| JP | 2005-98876 A | 4/2005 |
| JP | 2005-099662 A | 4/2005 |
| JP | 2007-20565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-2415 A | 1/2011 |
| JP | 2011-508219 A | 3/2011 |
| WO | 98/16814 A1 | 4/1998 |
| WO | 1998/016814 A1 | 4/1998 |
| WO | 1999/047963 A | 9/1999 |
| WO | 00/71991 A1 | 11/2000 |
| WO | 2000/066985 A1 | 11/2000 |
| WO | 2002/012864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2011108369 A1 | 9/2011 |
| WO | 2012/014778 A1 | 2/2012 |
| WO | 2013-024650 A1 | 2/2012 |
| WO | 2012/050011 A1 | 4/2012 |
| WO | 2012-144528 A1 | 10/2012 |

OTHER PUBLICATIONS

Extended European Search Report dated Oct. 20, 2014, issued in related EP Application No. 12770835.2 (10 pages).
Office Action dated Apr. 16, 2015, issued in related U.S. Appl. No. 13/946,091 (21 pages).
Office Action dated Apr. 24, 2015, issued in Chinese Patent Application No. 2012800041770.X, with English translation (27 pages).
Office Action dated Jun. 1, 2015, issued in Chinese Patent Application No. 201280005999.8, with English translation (15 pages).
Final Office Action dated Sep. 29, 2015, issued in corresponding U.S. Appl. No. 13/946,091 (23 pages).
Final Office Action dated Sep. 28, 2015, issued in corresponding U.S. Appl. No. 13/746,968 (24 pages).
Non-Final Office Action dated Nov. 16, 2015, issued in U.S. Appl. No. 14/178,442.
Advisory Action dated Feb. 2, 2016, issued in corresponding U.S. Appl. No. 13/946,091.
Chinese Office Action dated Jan. 25, 2016, issued in Chinese Application No. 201280005999.8.
International Search Report dated Mar. 15, 2016, issued in PCT/JP2015/084490.
Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, (p. 1612-1618).
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, (p. 1703-1713).
Chinese Office Action dated Aug. 13, 2013, issued in related Chinese application No. 201180011655.3; w/ English Translation (16 pages).
International Search Report dated Mar. 29, 2011, issued in related PCT/JP2011/053483.

(56) References Cited

OTHER PUBLICATIONS

International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report dated Mar. 29, 2011, issued in related PCT/JP2011/053482.
International Preliminary Report on Patentability (PCT/IPEA/409) issued in related PCT/JP2011/053482.
U.S. Office Action dated Jan. 3, 2013, issued in related U.S. Appl. No. 13/597,895.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry," Nucleic Acids Research, 1993, vol. 21, No. 4 (p. 803-806).
Keller, Richard et al., "Single-Molecule Fluorescence Analysis in Solution," Applied Spectroscopy, 1996, vol. 50, No. 7, (p. 12A-32A).
Lee, Yuan-Hsiang et al., "Laser-Induced Fluorescence Detection of a Single Molecule in a Capillary," Analytical Chemistry, dated Dec. 1, 1994, vol. 66, No. 23, (p. 4142-4149).
Li, Haitao et al., "Ultrasensitive Coincidence Fluorescence Detection of Single DNA Molecules," Analytical Chemistry, dated Apr. 1, 2003, vol. 75, No. 7, (p. 1664-1670).
Nie, Shuming et al., "Probing Individual Molecules with Confocal Fluorescence Microscopy," Science, dated Nov. 11, 1994, vol. 266, (p. 1018-1021).
Tahari, Abdel. "Fluorescence Correlation Spectroscopy: Ultrasensitive Detection in Clear and Turbid Media," University of Illinois, 2006, (p. 1-88).
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, (p. 2157-2159).
Itoh et al., "A New Method for Detection fo Influenza Viruses by Single Particle-Recognition Based on the Principle of Fluorescence Correlation Spectroscopy," Chemistry and Biology, 2009, vol. 47, No. 12, (p. 823-830).
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
International Search Report dated Feb. 14, 2012, issued in related PCT/JP2012/051175.
International Search Report dated Aug. 14, 2012, issued in related PCT/JP2012/067692.
U.S. Office Action dated Feb. 6, 2014, issued in related U.S. Appl. No. 13/946,091.
U.S. Office Action dated May 13, 2014, issued in related U.S. Appl. No. 13/946,091.
International Search Report dated Nov. 29, 2011, issued in related PCT/JP2011/072939.
Meyer-Almes, "Nanoparticle Immunoassays: A new Method for Use in Molecular Diagnostics and High Throughput Pharmaceutical Screening based on Fluorescence Correlation Spectroscopy", dit. R. Rigler, Springer, Berlin, 2000, pp. 204-224, cited in the Specification.
Kask et al., "Fluorescence-intensity distribution analysis and its application in biomolecular detection technology", PNAS, vol. 96, No. 24, Nov. 23, 1999, pp. 13756-13761; cited in the Specification.
Kato et al., "A single molecule analyzer that enable new analysis of DNA and protein interactions", Genome Medical Business Project, vol. 6, No. 2, 2002, pp. 271-277, cited in the Specification.
Kinjo, "Single molecule protein, nucleic acid, and enzyme assays and their procedures Single molecule detection by fluorescence correlation spectroscopy", Protein, Nucleic Acid, Enzyme, vol. 44, No. 9, 1999, pp. 1431-1438, w/ English translation, cited in the Specification.
International Search Report dated Aug. 28, 2012 issued in corresponding application No. PCT/JP2012/068947.
Extended European Search Report dated Mar. 31, 2015, issued in European Patent Application No. 12823870.6 (15 pages).
Extended European Search Report dated Apr. 10, 2015, issued in European Patent Application No. 12827023.8 (13 pages).
Office Action dated Mar. 25, 2015, issued in Chinese Patent Application No. 201280039905.9, with English translation (34 pages).
Extended European Search Report dated Oct. 2, 2017, issued in related European patent application No. 11750482.9.
Extended European Search Report dated Sep. 29, 2017, issued in related European patent application No. 11750483.7.
Related co-pending U.S. Appl. No. 15/983,412, filed May 18, 2018.
U.S. Non-Final Office Action dated Mar. 2, 2017, issued in U.S. Appl. No. 13/946,091.
Office Action dated Feb. 17, 2017, issued in Chinese Application No. 201280005999.8, with English translation (19 pages).
Bonnet et al., "Kinetics of conformational fluctuations in DNA hairpin-loops", Proc. Natl. Acad. Sci. USA, Jul. 1998, vol. 95, pp. 8602-8606, cited in Specification of PCT/JP2015/084490 (6 pages).
Official Action dated Nov. 24, 2016, issued in EP Patent Application No. 12823870.6. (9 pages).
U.S. Appl. No. 13/596,243, Mitsushiro Yamaguchi, filed Aug. 28, 2012.
U.S. Appl. No. 13/596,280, Mitsushiro Yamaguchi, filed Aug. 28, 2012.
U.S. Appl. No. 13/597,825, Mitsushiro Yamaguchi, filed Aug. 29, 2012.
U.S. Appl. No. 13/946,091, Tetsuya Tanabe, filed Jul. 19, 2013.
U.S. Appl. No. 14/178,442, Tetsuya Tanabe, filed Feb. 12, 2014.
Chinese Office Action dated Aug. 2, 2016 issued in Chinese Patent Application No. 201280005999.8 with Translation.
Office Action dated Mar. 20, 2019, issued in related EP Application No. 11 750 482.9 (6 pages).

* cited by examiner

FIG.1A
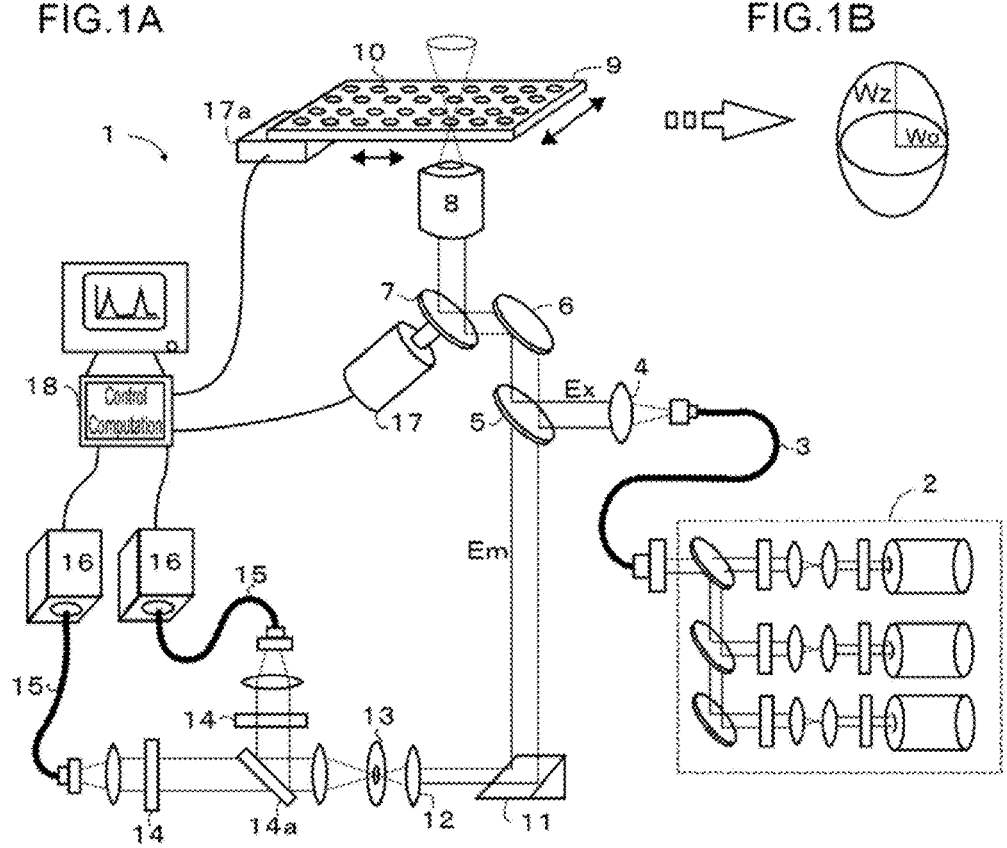
FIG.1B
FIG.1C
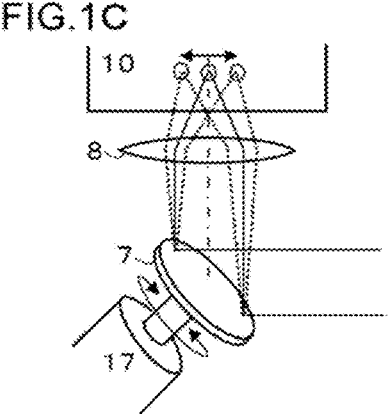
FIG.1D
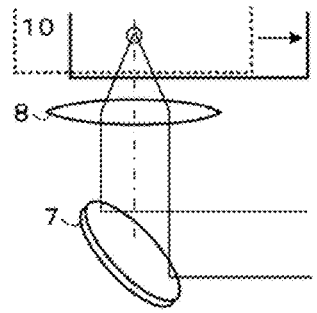

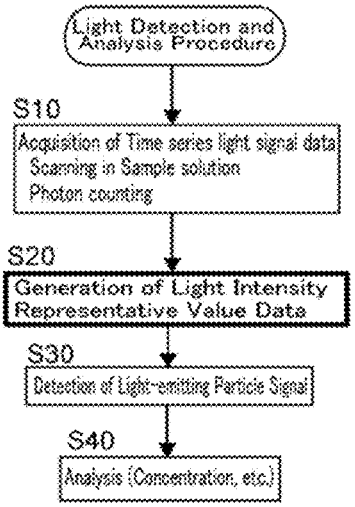
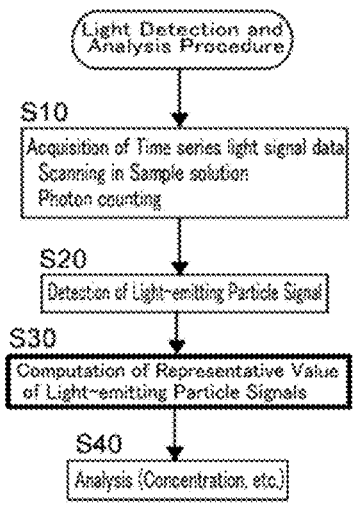
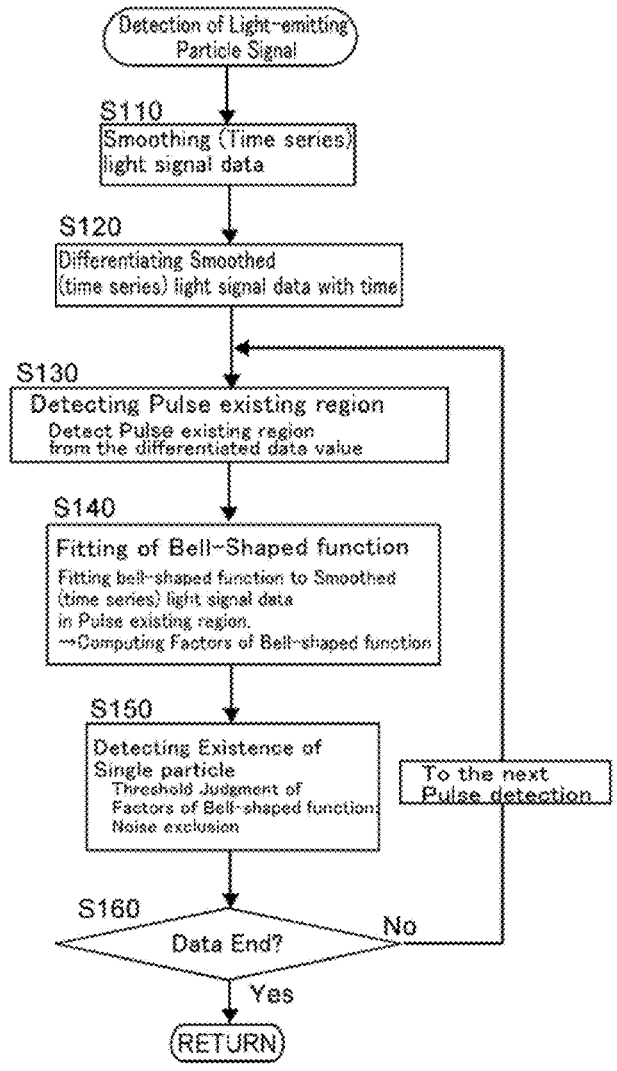

FIG. 5A
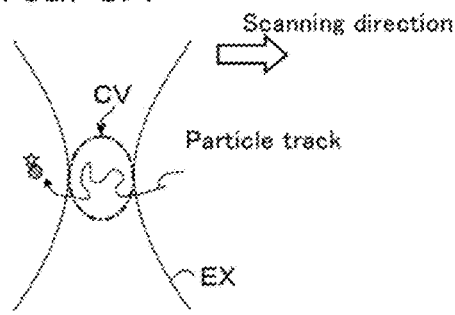
FIG. 5B
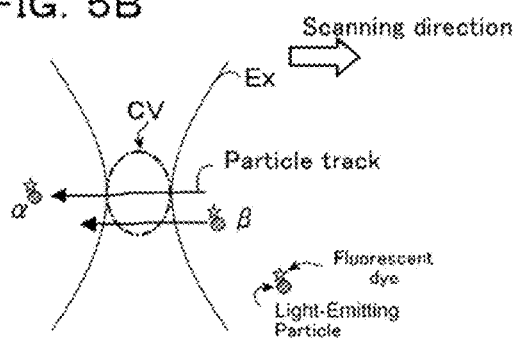
FIG. 5C
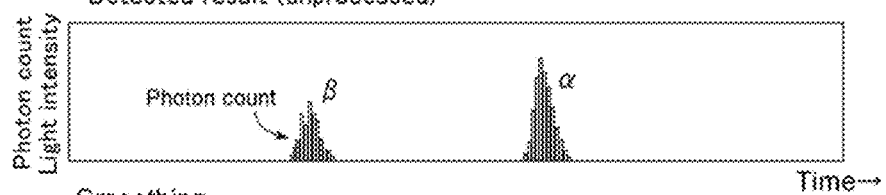
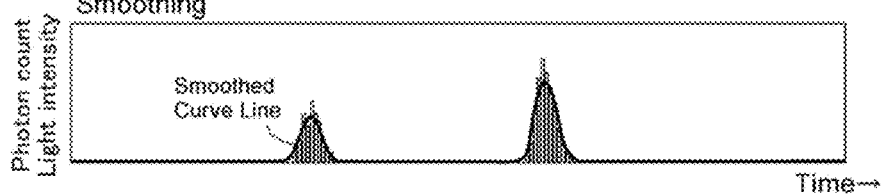
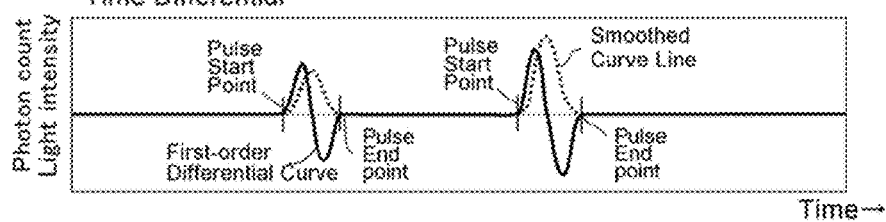
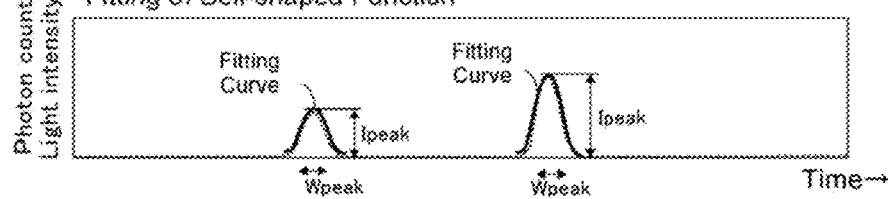

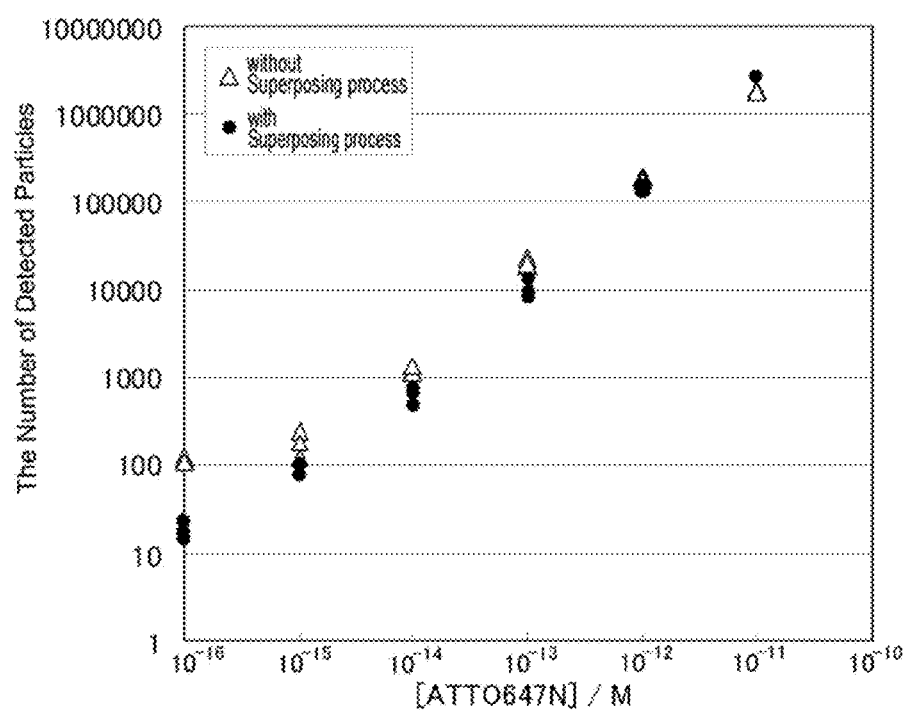
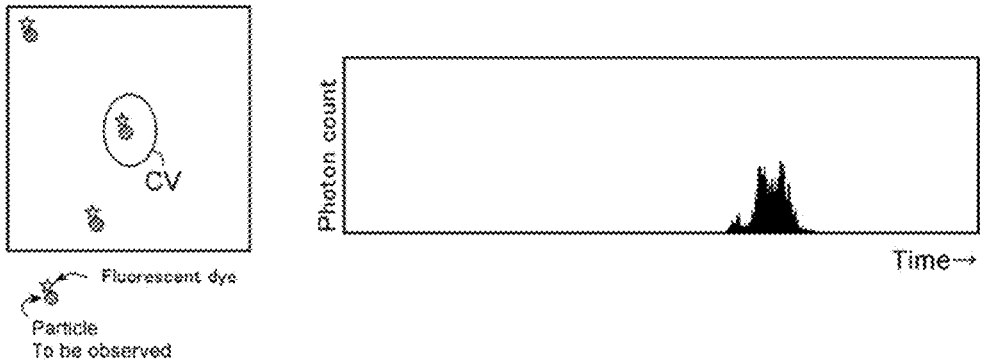

OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to an optical analysis device, optical analysis method and computer program for optical analysis, which detect individually the light from a single particle which emits light, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of L), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kinjo; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.

Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

In the above-mentioned scanning molecule counting method, together with the moving of the position of a light detection region in a sample solution, the light intensity value (or photon count value) measured sequentially is recorded as time series light intensity data, and in that data, an increase of the light intensity value indicating the light emitted from a light-emitting particle (a signal indicating light of a light-emitting particle) is detected. In that case, by analyzing, with the light intensity value, various characteristics of the light, such as a wavelength characteristic and a polarization characteristic, it becomes possible to detect the characteristics of the respective light-emitting particles and identify their kinds. For example, through dividing the detected light into two or more wavelength bands and referring to the ratio of the light intensity values detected in each of the wavelength bands, it becomes possible to detect a wavelength characteristic of the light emitted from a light-emitting particle. (see Japanese patent applications Nos. 2010-202995 and 2010-262267). Further, through dividing the detected light into polarized light components and referring to the ratio of the light intensity values detected in the respective polarized light components, it becomes to detect a polarization characteristic of the light emitted from a light-emitting particle and detect the motility characteristic of the light-emitting particle (see Japanese patent application No. 2010-234769)

However, the light measured in the above-mentioned scanning molecule counting method is faint light at the level of a single or several fluorescent molecule(s) and the measuring time of the light of one light-emitting particle is a short time during which the light-emitting particle is passing through the inside of a light detection region. Therefore, the light intensity value obtained from the detected light is low or the light amount or photon counts are small, and thus the scattering in the information on the wavelength characteristic, etc. of lights emitted from light-emitting particles becomes large, and it is possible that only detected results of low precision can be obtained.

Thus, the main object of the present invention is to provide a new optical analysis technique which suppresses the scattering in detected results, such as the wavelength characteristic etc. of the light emitted from a light-emitting particle obtained based on the light measured by the above-mentioned scanning molecule counting method, trying to improve the accuracy of the detected results.

Solution to Problem

In the present invention, briefly, by repetitively measuring the light emitted from the same light-emitting particle during making a light detection region pass through a predetermined route multiple times in the scanning molecule counting method as described above, it is tried to suppress the scattering and improve the detection accuracy in results of the detection of the existence of each light-emitting particle and/or its characteristic with the measured light intensity data.

Thus, according to one aspect of the present invention, the above-mentioned object is achieved by an optical analysis device which detects light from a light-emitting particle dispersed and moving at random in a sample solution using an optical system of a confocal microscope or a multiphoton microscope, comprising: a light detection region mover which moves a position of a light detection region of the optical system of the microscope along a predetermined route in the sample solution by changing an optical path of the optical system; a light detector which detects light from the light detection region; and a signal processor which generates time series light intensity data of the light from the light detection region detected with the light detector during moving the position of the light detection region in the sample solution and detects a signal indicating light from each light-emitting particle individually in the time series light intensity data; wherein the light detection region mover moves the position of the light detection region for at least two circulation times along the predetermined route, and the signal processor uses the time series light intensity data obtained during the moving of the position of the light detection region along the predetermined route for at least two circulation times to detect a signal indicating light from each light-emitting particle individually.

In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Further, in the followings in this specification, "a signal" of a light-emitting particle means a signal expressing light from a light-emitting particle, unless noted otherwise.

As understood from the above, in the basic structure of the present invention, i.e., the scanning molecule counting method, the light detection is sequentially performed while the position of the light detection region is moved in a sample solution, namely, while the inside of the sample solution is scanned with the light detection region, by changing the optical path of the optical system of the microscope. Then, when the light detection region moving in the sample solution encompasses a randomly moving light-emitting particle, the light from the light-emitting particle is detected by the light detector, and thereby, it is expected that the existence of one particle will be detected.

Thus, in the sequentially detected light, a signal indicating light from a light-emitting particle is individually detected, and thereby, the existences of individual particles are detected one by one, and accordingly, diverse information on the conditions of the particles in the solution will be acquired. In that case, since, as already noted, the light of a light-emitting particle is weak and can be detected only in a short time from its entry into the moving light detection region to its exit therefrom, a light amount or a photon count, detected when the light detection region has passed through the region where a light-emitting particle exists only once, is relatively small, and therefore, the information acquired from such a light amount or photon count can be largely scattered and of low accuracy. Then, in the present invention, as described above, the light detection region mover makes the light detection region circulates along the predetermined route by moving the position of the light detection region for at least two circulation times along the predetermined route, and detects multiple times the light from each light-emitting particle which exists in the predetermined route to acquire more light amount or photons from each light-emitting particle, and thereby it is tried to achieve the reduction of the scattering and the accuracy improvement in the detection of the existence of a light-emitting particle (The detection of a signal is the detection of the existence of a light-emitting particle.) and the information obtained from the signals.

The moving of the position of the light detection region in the sample solution by changing the optical path of the optical system of the microscope may be conducted in an arbitrary way. For example, changing the optical path of the optical system of the microscope to change the position of the light detection region may be performed using a galvanometer mirror adopted in a laser scan type light microscope. The above-mentioned predetermined route may be a circulating route (closed route) of an arbitrary shape, for example, is chosen from circular, elliptical and rectangular ones. According to the manner of changing the position of the light detection region by changing the optical path of the optical system of the microscope, the moving of the light detection region is quick, and since neither mechanical vibration nor hydrodynamic action occurs substantially in the sample solution, it is advantageous to enable a measurement under a stable condition without a light-emitting particle to be an object to be detected being influenced by a dynamic action.

Moreover, in the structure of the above-mentioned inventive device, if a light-emitting particle moving at random deviates, owing to the diffusional motion, from the predetermined route during the circulating of the light detection region along the predetermined route, it becomes impossible to detect the light from the light-emitting particle multiple times. Thus, in the inventive device, preferably, the position of the light detection region is moved with a cycle time shorter than the diffusion time until a light-emitting particle deviates owing to the diffusion from the predetermined route. In this regard, it should be noted that the moving cycle time of the position of the light detection region is dependent not only on the moving speed of the light detection region but the length of the predetermined route. Thus, the length of the predetermined route and the moving speed of the light detection region may be adjusted appropriately so that the light detection region can circulate through the predetermined route with a cycle time shorter than the diffusion time until a light-emitting particle to be observed deviates from the predetermined route. Furthermore, preferably, the moving speed of the position of the light detection region in the sample solution is set higher than the diffusion moving velocity of the light-emitting particle to be an object to be detected (the average moving speed of the particles by the Brownian motion). If the moving speed of the position of the light detection region in the sample solution is lower than the diffusion moving velocity of a light-emitting particle, the position of the light-emitting particle, even during being encompassed in the light detection region, can move at random owing to the Brownian motion. And in that case, the light intensity of the light-emitting particle can change at random, causing the reduction of the detection accuracy (the detected light intensity of a light-emitting particle changes depending upon the positions of the light-emitting particle in the light detection region.). In this regard, when the diffusion speed of a light-emitting particle to be measured is too quick so that each particle cannot be observed twice or more as it is, the viscosity of the sample solution may be increased so that the translational diffusion velocities of particles will be reduced. The viscosity of the sample solution can be adjusted by adding thickeners or gelatinizers (polymer compounds, polysaccharides, silicones, glycerol, PEG, dextrans, sucrose, sodium arginine, polysilicon, water-soluble cellulose, etc.).

Furthermore, in the structure of the above-mentioned inventive device, it is preferable that, after the end of the predetermined number of times of the circulating movements of the position of the light detection region along the predetermined route, the processes from the photon detection to the generation of time series light intensity data are performed in the above-mentioned manner in a different place in the sample solution through moving the stage of the microscope to move the sample solution so that more number of signals of light-emitting particles are detectable. When the predetermined route length is made short in order to make the cycle time of the circulating movement of the light detection region shorter than the diffusion time until a light-emitting particle deviates owing to diffusion from the predetermined route as already noted, the number of the light-emitting particles existing in one predetermined route would be decreased. And, as the number of the detected light-emitting particles becomes smaller, the accuracy of the information acquired from the signals of light-emitting particles would deteriorate also. Then, in one manner of the present invention, the light detection as described above is conducted in a plurality of different positions in the sample solution so that the detected number of light-emitting particles will be increased, and thereby, it is tried to achieve the improvement of the accuracy of the information acquired from the signals of light-emitting particles. Thus, the inventive device may be further designed such that, the position of the sample solution is moved each time of the end of the moving of the position of the light detection region along the predetermined route of a predetermined number of circulations, and moving the position of the light detection region of the optical system in the sample solution along the predetermined route for at least two circulation times by changing the optical path of the optical system with the light detection region mover; detecting the light from the light detection region with the light detection portion; and generating time series light intensity data with the signal processor are repeated on the position of the sample solution after the moving, and then for each position after moving the sample solution, individual detection of the signals indicating light from the respective light-emitting particles existed in the predetermined route in time series light intensity data is conducted. In other words, according to this manner, through combining the circulating motion of the light detection region by changing the optical path of an optical system with the intermittent moving of the sample solution, it becomes possible to conduct more accurately the detection of the existence(s) of (a) light-emitting particle(s) and the acquisition of the information obtained from its (those) signal(s). In this regard, preferably, as already noted, the moving of the sample solution may be conducted by moving the container of the sample solution with the moving of the stage of the microscope. In that case, it is thought that, since no flow does occur in the solution, the light-emitting particle on the sample solution is less influenced.

In the above-mentioned inventive device, generally, the detection of signals of a light-emitting particle from the generated time series light intensity data and the extraction of a characteristic of the signals may be conducted through either of two manners.

In the first manner, the light intensity data measured during the light detection region circulating along the predetermined route (time series light intensity data) is considered to be data obtained by connecting data of performing the light intensity measurements multiple times in one predetermined route, and for each position on the predetermined route, the representative value, for example, the average, the median, the minimum, the maximum or the mode of those light intensity values is determined with reference to two or more light intensity values corresponding to each position in time series light intensity data, and thereby, time series light intensity representative value data, consisting of the representative values of light intensity values, is generated. Here, usually, the moving speed of a light detection region is set to be constant or the moving speeds on passing the same position on the predetermined route in the respective circulations of a light detection region is set to be mutually equal, and thus, the position in the predetermined route corresponds to the time from the start time point of each circulation in time series light intensity data. Thus, concretely, it may be designed that the representative value of light intensity values is determined in each time point from the start point in each circulation in time series light intensity data, and the time series light intensity representative value data is generated by aligning in time series the representative values of the light intensity values. Then, in the time series light intensity representative value data, a signal indicating light from each light-emitting particle is detected individually, and a characteristic quantity of the signal (namely, a property of the signal) is detected.

In the second manner of the detection of signals of a light-emitting particle, and the extraction of the characteristic of the signals, first, a signal indicating light from each light-emitting particle is detected individually in the time series light intensity data, and the characteristic quantities of the signals are detected, respectively. In the group of those detected signals of light-emitting particles, the signals of the light-emitting particles, which exist in the predetermined route, of the number corresponding to the circulation times are included, and therefore, with reference to the detected signals for each of the light-emitting particles, the representative value of the characteristic quantity of signals is computed. Namely, for the second manner, the signal processor detects individually signals indicating light from the respective light-emitting particles in time series light intensity data, and detects the characteristic quantity of each signal, and then, the representative value, for example, the average, the median, the minimum, the maximum or the mode of the characteristic quantities of signals is computed for each light-emitting particle.

The above-mentioned characteristic quantity of a signal, typically, may be a light intensity or a photon count, and in a case that two or more components are detected as detected lights, the characteristic value of a signal may be an index value indicating an arbitrary characteristic of a light-emitting particle, such as a polarization degree, a rotational diffusion constant, an emission spectrum, obtained from the ratio of light intensities or photon counts of two or more components.

In the processes of the signal processor of the above-mentioned inventive device, the judgment of whether or not one light-emitting particle enters into the light detection region from a signal in the successively detected values from the light detector may be performed based on the shape of the signal in the time series light intensity data. In an embodiment, typically, it may be designed that the entry of one light-emitting particle into a light detection region is detected when a signal with a larger intensity than a predetermined threshold value is detected. More concretely, as explained in the following column of embodiments, usually, a signal indicating light from a light-emitting particle appears as a bell-shaped pulse form signal having an intensity beyond a certain degree in the time series detected values, i.e., light intensity data, of the light detector, while a noise is not of bell-shaped pulse form, or appears as a signal with a small intensity. Then, the signal processor of the inventive device may be designed to detect on time series light intensity data (or time series light intensity representative value data) a pulse form signal which has an intensity exceeding a predetermined threshold value as a signal indicating light from a single light-emitting particle. The "predetermined threshold value" can be experimentally set to an appropriate value.

Furthermore, the object to be detected in the inventive device is the light from a single light-emitting particle, and thus, light intensity is extremely weak, and when one light-emitting particle is a single fluorescent molecule or several molecules, the light is stochastically emitted from the light-emitting particle, so that minute time gaps can be generated in the signal values. If such a gap is generated, the identification of a signal corresponding to the existence of one light-emitting particle will become difficult. Then, the signal processor may be designed to smooth time series light intensity data to process the data so that minute time gaps in signal values can be ignored, and to detect as a signal indicating light from a single light-emitting particle a bell-shaped pulse form signal having an intensity beyond a predetermined threshold value in the smoothed time series light intensity data.

In one of manners of the above-mentioned present invention, the number of light-emitting particles encompassed in the light detection region may be counted by counting the number of the selectively detected signals (The counting of particles). In that case, by associating the number of the detected light-emitting particles with the moving amount of the position of the light detection region, the information on the number density or concentration of the light-emitting particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the light-emitting particle can be concretely computed.

The processes of the optical analysis technique of conducting a light detection with moving the position of a light detection region in a sample solution and detecting the signal from each light-emitting particle individually in the above-mentioned inventive device, in which the reduction of the scattering and the improvement of the accuracy in the detection of the existence of a light-emitting particle and the information acquired from its signal are tried by conducting the circulating movement of a light detection region along a predetermined route to detect light from a light-emitting particle in the predetermined route multiple times, can be realized with a general-purpose computer. Thus, according to another aspect of the present invention, there is provided a computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising: moving a position of a light detection region of the optical system along a predetermined route for at least two circulation times by changing the optical path of the optical system; detecting light from the light detection region and generating time series light intensity data during the moving of the position of the light detection region along the predetermined route for the at least two circulation times; and detecting individually a signal indicating light from each light-emitting particle existing in the predetermined route using the time series light intensity data. In this regard, the computer program is provided with being stored in a computer readable storage medium. The computer reads out the program memorized in the storage device and realizes the above-mentioned procedures by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

Also in this computer program, preferably, the position of the light detection region is moved along the predetermined route in a cycle time shorter than a diffusion time until a light-emitting particle deviates from the predetermined route by diffusion. In that case, for the moving of the position of the light detection region within the sample solution by changing the optical path of the optical system, for example, the optical path of the optical system of the microscope may be changed to change the position of the light detection region using a galvanometer mirror adopted in a laser scan type light microscope, and the predetermined route may be chosen from the circulating routes of arbitrary shapes, such as circular, elliptical, rectangular ones. Also, preferably, the moving speed of the position of the light detection region in the sample solution is set to be higher than the diffusion moving velocity of a light-emitting particle to be an object to be detected, in order to avoid a random intensity change of the light of the light-emitting particle. Furthermore, in the above-mentioned computer program preferably, a step of moving the position of the sample solution by moving the stage of the microscope each time of the end of the predetermined number of circulations of the moving of the position of the light detection region along the predetermined route is comprised, and in the position of the sample solution after the moving, the light detection region circulating movement step and time series light intensity data generation step are repeated, and the light-emitting particle signal detection step is performed for each of the positions of the sample solution after the moving, and thereby, more signals of light-emitting particles are detectable.

In the signal processes in the above-mentioned computer program, similarly to the case of the inventive device, a step of generating time series light intensity representative value data consisting of a representative value of the light intensity values determined for each position in the predetermined route in time series light intensity data may be performed, and in the light-emitting particle signal detection step, it may be designed that a signal indicating light from each of the light-emitting particles is detected individually in the time series light intensity representative value data and the characteristic value of each of the signals is detected (The first manner), or in the light-emitting particle signal detection step, it may be designed that a signal indicating light from each light-emitting particle is detected individually in time series light intensity data; the characteristic value of each of signals is detected; and the representative value of the characteristic values of the signals is computed for each light-emitting particle (The second manner). The characteristic value of a signal may be at least one chosen from the group of a light intensity, a photon count, a polarization degree, a rotational diffusion constant and an emission spectrum.

Moreover, in the above-mentioned computer program, individual detection of a signal indicating light from each light-emitting particle may be performed based on the shape of the time series signals. In one embodiment, typically, it may be designed that the entry of one light-emitting particle into the light detection region is detected when a signal with a larger intensity than a predetermined threshold value is detected. Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle.

Also in this computer program, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

According to the above-mentioned inventive device or computer program, there is realized a novel optical analysis method of detecting the light of each light-emitting particle with moving the position of the light detection region in a sample solution, in which the reduction of the scattering and the improvement of the accuracy in the detection of the existence of a light-emitting particle and the information acquired from its signal are tried by conducting the circulating movement of a light detection region along a predetermined route to detect light from a light-emitting particle in the predetermined route multiple times. Thus, according to the present invention, there is provided an optical analysis method of detecting light from a light-emitting particle dispersed and moving at random in a sample solution using an optical system of a confocal microscope or a multiphoton microscope, comprising: a light detection region circulating movement step of moving the position of a light detection region of an optical system of the microscope in the sample solution for at least two circulation times along a predetermined route by changing the optical path of the optical system; a time series light intensity data generation step of detecting the light from the light detection region during the moving of the position of the light detection region along the predetermined route for the at least two circulation times and generating time series light intensity data; and a light-emitting particle signal detection step of detecting individually a signal indicating light from each light-emitting particle which exists in the predetermined route using the time series light intensity data.

In this method, also, the predetermined route may be chosen from the circulating routes of arbitrary shapes, such as circular, elliptical, rectangular ones, and typically, the position of the light detection region is moved along the predetermined route in a cycle time shorter than a diffusion time until a light-emitting particle deviates owing to diffusion from the predetermined route by using a galvanometer mirror adopted in a laser scan type light microscope, and especially, preferably, the moving speed of the position of the light detection region in the sample solution is set to be higher than the diffusion moving velocity of a light-emitting particle to be an object to be detected. Furthermore, a step of moving the position of the sample solution each time of the end of the predetermined number of circulations of the moving of the position of the light detection region along the predetermined route may be comprised, and in the position of the sample solution after the moving, the light detection region circulating movement step and time series light intensity data generation step may be repeated, and the light-emitting particle signal detection step may be performed for each of the positions of the sample solution after the moving, so that more signals of light-emitting particles are detectable.

Further, in the signal processing, similarly to the case of the inventive device, a step of generating time series light intensity representative value data consisting of a representative value of the light intensity values determined for each position in the predetermined route in time series light intensity data may be comprised, and in the light-emitting particle signal detection step, it may be designed that a signal indicating light from each of the light-emitting particles is detected individually in the time series light intensity representative value data and the characteristic value of each of the signals is detected (The first manner), or in the light-emitting particle signal detection step, it may be designed that a signal indicating light from each light-emitting particle is detected individually in time series light intensity data; the characteristic value of each of signals is detected; and the representative value of the characteristic values of the signals is computed for each light-emitting particle (The second manner). The characteristic value of a signal may be at least one chosen from the group of a light intensity, a photon count, a polarization degree, a rotational diffusion constant and an emission spectrum.

Moreover, in the above-mentioned method, individual detection of a signal indicating light from each light-emitting particle may be performed based on the shape of the time series signals. In one embodiment, typically, it may be designed that the entry of one light-emitting particle into the light detection region is detected when a signal with a larger intensity than a predetermined threshold value is detected. Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle.

Also in this method, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a complex, a micelle, a metallic colloid, a plastic bead, etc.), and it should be understood that such a case belongs to the scope of the present invention also.

Effect of Invention

In the scanning molecule counting method to which the present invention is directed, basically, by capturing the light from a light-emitting particle when the light detection region moving in a sample solution encompasses the light-emitting particle, the detection of the existence of the light-emitting particle and/or its characteristic will be achieved. Thus, it is difficult to follow one light-emitting particle and continue detecting the light, and thus, the observing time of one light-emitting particle is short so that the light amount or photon count from a light-emitting particle will be small, and thereby, the scattering in the information acquired therefrom tends to be large. However, according to the present invention, since it becomes possible to measure the light from one light-emitting particle multiple times by circulating the same predetermined route, an improvement in the detection accuracy of the light amount or photon count from a light-emitting particle and the reduction of the scattering in the information acquired therefrom are expected. Moreover, as shown in the below-mentioned embodiments, according to one manner of the present invention, the magnitude of background noise is reduced relatively to a signal of a light-emitting particle and an improvement of the S/N ratio is achieved.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the scanning molecule counting method according to the present invention is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism which moves the horizontal position of a micro plate to move the position of a sample solution.

FIGS. 2A and 2B are a schematic diagram explaining the principle of the light detection and a schematic diagram of the variation of the measured light intensity with time in the scanning molecule counting method to which the present invention is applied, respectively. FIG. 2C is a drawing explaining about the manner of moving the position of the light detection region along one scanning track (the predetermined route) in the present invention. FIG. 2D is a drawing explaining about the manner of moving the position of a sample solution.

FIGS. 3A-3E is a drawing explaining about the manner of the signal processing of time series light intensity data in the present invention. FIG. 3A is a schematic diagram of time series light intensity data in a case of carrying out the circulating movement of a light detection region in one scanning track (predetermined route) as shown in FIG. 3B. FIG. 3C explains about a manner of referring to time series light intensity data obtained in each circulation of the light detection region in the time series light intensity data of FIG. 3A at each time measured from the time point (t0, t3, t6) of passing through the starting point s0 of the circulation of the light detection region and determining, as shown in FIG. 3D, the representative values in the data of all the circulations referred to. FIG. 3E explains about a manner of detecting light-emitting particle signals in the whole time series light intensity data of FIG. 3A first and then determining the representative values of signals for each light-emitting particle ($\alpha$, $\beta$).

FIGS. 4A-4C are diagrams showing the procedures of the scanning molecule counting method performed in accordance with the present invention in the form of flow chart. FIG. 4A is procedures in a case of detecting a signal after generating time series light intensity representative value data; and FIG. 4B is procedures in a case of computing the representative value of the signal for each light-emitting particle after detecting signals. FIG. 4C is procedures of detecting a light-emitting particle signal in time series light intensity data or time series light intensity representative value data.

FIGS. 5A and 5B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 5C shows drawings explaining an example of the signal processing step of the detected signals in the procedure for detecting the existence of a light-emitting particle from the measured time series light intensity data (change in time of photon count) in accordance with the scanning molecule counting method.

Figure 2A:
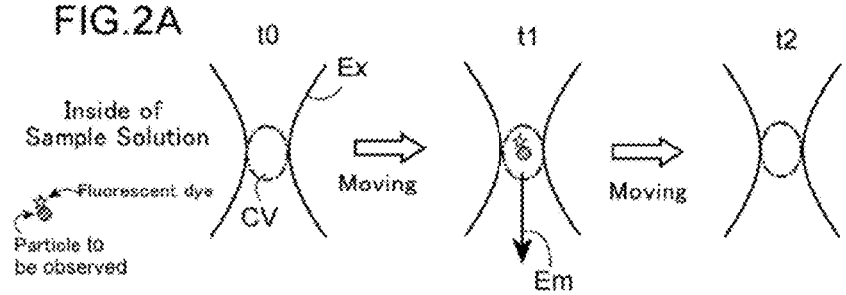

FIG. 10 shows the numbers of signals of light-emitting particles obtained by the scanning molecule counting method using sample solutions of various light-emitting particle concentrations. • indicates the number of particles detected on time series light intensity representative value data, which is the average of time series light intensity data of three circulations, and Δ indicates the number of particles detected on time series light intensity data of one circulation.

FIG. 11 show examples of the time variation of the photon count (light intensity) obtained in a conventional optical analysis technique computing fluorescence intensity fluctuation, where FIG. 11A shows a case that the particle concentration is at a level providing a sufficient precision in the measurement, and FIG. 11B shows a case that the particle concentration in a sample is significantly lower than the case of FIG. 11A.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
14a - - - Dichroic mirror or Polarization beam splitter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

Structure of Optical Analysis Device

In the basic structure, an optical analysis device which realizes the optical analysis technique according to the present invention is a device constructed by associating the optical system of a confocal microscope and a photodetector, enabling FCS, FIDA, etc., as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically fluorescent particles or particles to which a light emitting label such as a fluorescent dye is attached, are dispersed or dissolved, and when such a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13; transmits through the barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with a Gaussian type distribution having the peak at the center of the region. The effective volume is a volume of an approximate ellipsoid bordering a surface where the light intensity is reduced to $1/e^2$ of the peak intensity.), which focal region is called as "confocal volume". Furthermore, in the present invention, since the light from a single light-emitting particle, for example, the faint light from one fluorescent dye molecule is detected, preferably, a super high sensitive photodetector, usable for the photon counting, is used for the photodetector 16. When the detection of light is performed by the photon counting, the measurement of light intensity is performed for a predetermined time in a manner of measuring the number of photons which have sequentially arrived at a photodetector in every predetermined unit time (BIN TIME). Thus, in this case, the time series light intensity data is time series photon count data. Also, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, quick measurement can be achieved even when there are two or more specimens.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the type of changing an optical path to move the absolute position of a light detection region). This mirror deflector 17 may be the same as that of a galvanomirror device equipped on a usual laser scan type microscope. Furthermore, as illustrated in FIG. 1D, the stage position changing apparatus 17a is operated in order to move the horizontal position of the container 10 (micro plate 9), into which the sample solution has been dispensed, to move the relative position of the light detection region in the sample solution (the type of moving the position of a sample solution). As explained in detail later, in the present invention, the light detection region is moved to circulate along a scanning track (a predetermined route) by the above-mentioned type of moving the absolute position of the light detection region by changing optical path, and when the number of circulations has reached to the predetermined number of times, the place in which the circulating movement of the light detection region is conducted in the sample solution is changed by the type of moving the position of a sample solution. In either of the ways, in order to attain a desired moving pattern of the position of the light detection region, the mirror deflector 17 or the stage position changing apparatus 17a is driven in harmony with the light detection of the photodetector 16 under the control of the computer 18. The scanning track of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 or stage up and down.

In the case that a light-emitting particle to be an object to be observed emits light by multiple photon absorption, the above-mentioned optical system is used as a multiphoton microscope. In that case, since the light is emitted only from the focal region of the excitation light (light detection region), the pinhole 13 may be removed. Further, in the case that a light-emitting particle to be an object to be observed emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, it may be designed to divide a detected light into two or more wavelength bands by inserting a dichroic mirror 14a in a detected light optical path, and detect them independently with two or more photodetectors 16. According to this structure, it becomes possible to detect the information on the emission wavelength characteristic (emission spectrum) of a light-emitting particle or detect the lights of two or more kinds of light-emitting particles, when contained, independently in accordance with the wavelengths. Moreover, with respect to the light detection, it may be designed to use light, polarized in a predetermined direction, as excitation light and detect separately components of detected light in the direction of the excitation light and the direction perpendicular thereto, so as to detect the polarization characteristics of the light of a light-emitting particle. In that case, a polarizer (not shown) is inserted in an excitation light optical path, and a polarization beam splitter 14a is inserted in a detected light optical path. (see embodiment 3).

The computer 18 has a CPU and a memory, and the inventive procedures are performed through the CPU executing various operational processes. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc., or the above-mentioned program may be distributed to a computer through communication line, and the computer which received this distribution may be made to execute the program.

The Principle of the Inventive Method

As described in the column of "Summary of Invention", briefly, according to the inventive optical analysis technique, in the scanning molecule counting method, by moving a light detection region to circulate it along a predetermined route multiple times and repetitively measuring the light emitted from the same light-emitting particle during the circulations, it is tried to achieve the suppression of the scattering and the improvement in the detection accuracy in the detection of the existence of each light-emitting particle and/or its characteristic by means of the measured light intensity data. In the following, the principle of the scanning molecule counting method; the manner of the circulating movement of a light detection region in the present invention; and the schema of the signal processing of the measured light intensity data are explained.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques, such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 11A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn in FIG. 11B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring time should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

Figure 2B:
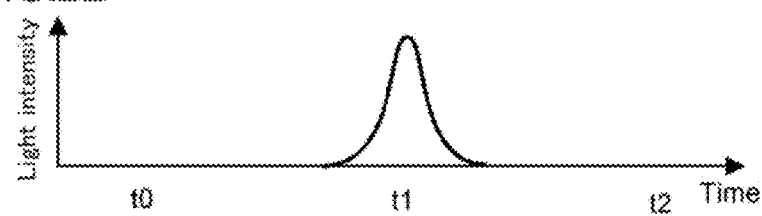

As the processes to be performed in the scanning molecule counting method, briefly speaking, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2A. Then, for example, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. Moreover, from the signal intensities, the various characteristics of the light of light-emitting particles and the characteristics of a light-emitting particle itself become detectable for the respective light-emitting particles. In the principle of the scanning molecule counting method, no statistical calculation processes, such as the calculation of the fluorescence intensity fluctuation, are conducted and the light-emitting particles are one by one detected, and therefore, the information about the concentration or number density, characteristics of the particle is acquirable even in a sample solution with a low particle concentration at the level where no sufficiently accurate analysis is available in FCS, FIDA, etc.

2. Circulating Movement of Light Detection Region

In the above-mentioned scanning molecule counting method, since the light amount which a light-emitting particle emits is typically at a level of the light amount emitted by one to several fluorescent dye molecules, it is extremely weak, and further, since the light of a light-emitting particle is detected only when the light detection region moving in a sample solution encompasses the light-emitting particle, the light amount or the photon count obtained from a light-emitting particle is extremely small when the light detection region encompasses one light-emitting particle only once, and therefore, the detection accuracy of the light of a light-emitting particle can be low, or the scattering in the information about the wavelength characteristic acquired from the light of a light-emitting particle can be large. Then, in the present invention, as already noted, the above-mentioned light measurement is performed during conducting multiple times of the circulating movements of a light detection region along a predetermined route in a sample solution, and light from the same light-emitting particle existing in the predetermined route is detected multiple times so that the light amount from one light-emitting particle will be increased, and thereby, it is tried to achieve the improvements in the accuracy of the detection of the existence of a light-emitting particle and the detection of the characteristic of the light of the light-emitting particle or the light-emitting particle itself.

Figure 2C:
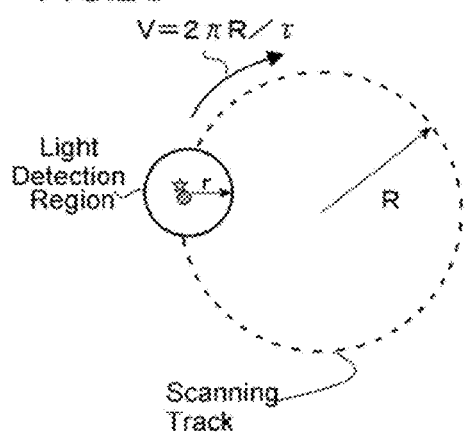

FIG. 2C is a drawing schematically showing a manner of circulating a light detection region along a scanning track (predetermined route) multiple times. With reference to the drawing, in the present invention, first, the mirror deflector 17 of FIG. 1 is driven to change the optical path so that the absolute position of the light detection region will be circulated along the predetermined route (scanning track). During this circulating movement of the light detection region, if the light-emitting particle in the scanning track hardly changes its position, whenever the light detection region passes through the region occupied by the light-emitting particle, the light of the light-emitting particle is measured, and therefore, it becomes possible to obtain a larger light amount from the light-emitting particle. And if the light amount from one light-emitting particle increases, improvements of the detection accuracy in the detection of the existence of a light-emitting particle and characteristics of the light of the light-emitting particle or the light-emitting particle itself are expected.

In this regard, in order to detect the light from the same light-emitting particle for two or more circulations, the circulating movement of the light detection region of the desired number of times should be achieved before the light-emitting particle deviates from the scanning track by the diffusional moving. Thus, in the present invention, preferably, the moving cycle of the light detection region is set to be shorter than the diffusion time until a light-emitting particle deviates from the scanning track by diffusion. Concretely, an average square displacement $<x^2>$ owing to the translational diffusion of a light-emitting particle having the diffusion constant D in a duration t is given by:

$$<x^2>=6Dt \quad (1),$$

and, the time until the light-emitting particle deviates from the light detection region having radius r, becomes approximately $$t \sim 4r^2/6D \quad (2)$$

Therefore, the moving cycle τ of a light detection region should be set so that $$\tau < t \sim 4r^2/6D \quad (3)$$

can be surely established. That is, for example, supposing a scanning track is a circle of radius R, the moving speed V will be determined to be $$V=2\pi R/\tau > 2\pi R/(4r^2/6D) \quad (4).$$

Since the radius of a light detection region is usually 0.2~30 μm, the moving cycle τ should just be shorter than 6 sec. for a light-emitting particle having the diffusion constant D of $2 \times 10^{-10} \sim 10 \times 10^{-11}$ [m$^2$/s]. Further, in a case that the diameter of a light detection region is 1.6 μm and the diffusion constant of a light-emitting particle is $1.7 \times 10^{-10}$ [m$^2$/s], the moving cycle τ needs to be less than 10 ms. Thus, in an actual case, in order that the moving cycle of the light detection region does not exceed the upper limit determined from the diffusion constant D of a light-emitting particle, the radius r of a light detection region or the radius R of a scanning track, the moving speed V of the light detection region and the route length of the scanning track (or the radius R of the scanning track) are selected.

Figure 2D:
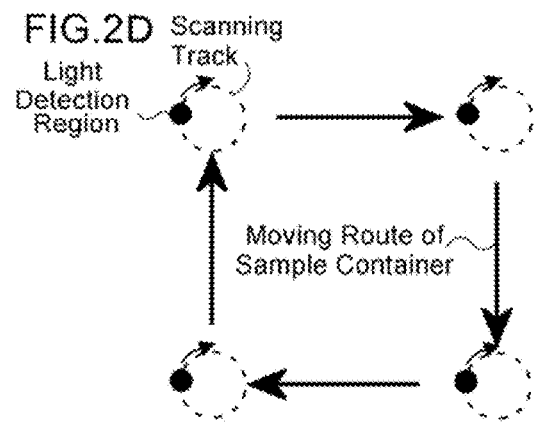

In this regard, as noted above, in the manner of circulating a light detection region around one scanning track before a light-emitting particle deviates from the scanning track, the light-emitting particles which can be detected are limited only to the light-emitting particles in the scanning track. Thus, the shorter the route length of a scanning track is, the smaller the number of the detected light-emitting particles is, and as the number of the light-emitting particles is smaller, the scattering increases and the accuracy also deteriorates in the detected values with respect to various characteristics obtained from the light-emitting particle signals. Then, in order to increase the number of detected light-emitting particles, whenever the predetermined number of times of the circulations of the light detection region along the scanning track are completed, the position of a sample solution may be moved, for example, by driving the stage position changing apparatus 17a, as schematically shown in FIG. 2D, and the circulating movement of the light detection region may be repeated in the position after the moving. In that case, since it is just enough that the moving length is longer than the diameter of the light detection region, typically, the moving length is 1 µm or more. Further, the route for the position of the sample solution may also be a circulating route, and in that case, its cycle time may be set to be longer than the diffusion time until a light-emitting particle deviates from the scanning track by diffusion. (This is for detecting the light of a light-emitting particle other than the light-emitting particle whose light has been already measured.).

3. Signal Processing of Light Intensity Data

Figure 3A:
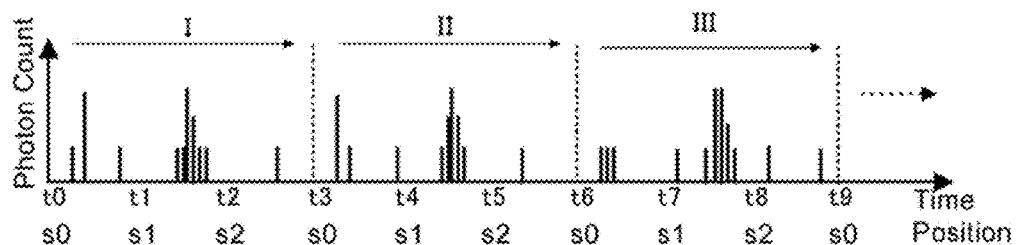

In the scanning molecule counting method, by conducting the light measurement with moving a light detection region, time series light intensity data are generated. And in a manner as explained in detail later, a signal indicating light of a light-emitting particle is detected individually on time series light intensity data. In this connection, as noted above, when the cycle time of the circulating movement of a light detection region is set shorter than the diffusion time until a light-emitting particle deviates from a scanning track by diffusion, time series light intensity data periodically exhibits the light intensities or photon counts detected when the light detection region passes through the scanning track as shown in FIG. 3A. Namely, in the case of the example of FIG. 3A, the sections I, II and III are the light intensities or the photon counts of the circulating movements along the scanning track of the light detection region of the first, the second and the third circulations, respectively. And, when the speed in the circulating movement of the light detection region is constant, or always the same in the same site on the scanning track, the time of time series light intensity data periodically corresponds to the position on the scanning track. In the case of the illustrated example, the time points t0, t3, t6 and t9 in time series light intensity data correspond to the position s0 of the scanning track in FIG. 3B, the time points t1, t4 and t5 in time series light intensity data correspond to the position s1 of the scanning track; and the time points t2, t5 and t8 in time series light intensity data correspond to the position s2 of the scanning track. Therefore, it can be assumed that the light of a light-emitting particle on a scanning track appears almost periodically in time series light intensity data at the time corresponding to the same position of the scanning track. Considering this, the detection of a signal of a light-emitting particle from time series light intensity data obtained during the circulating movement of a light detection region on a scanning track may be conducted in accordance with either of the following two manners.

Figure 3C:
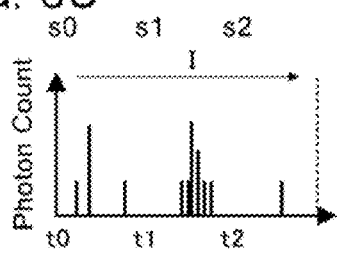
Figure 3B:
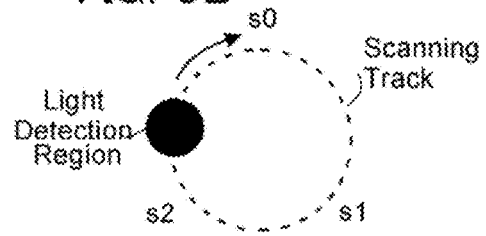
Figure 3D:
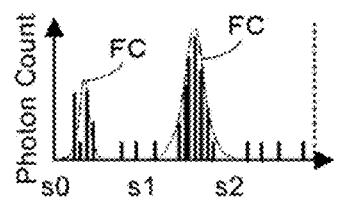

For the first manner, as schematically drawn in FIG. 3C, time series light intensity data as in FIG. 3A is divided into sections of the respective moving cycles of a light detection region; for each time from the start point of each section, with reference to the light intensities or photon counts in the corresponding times in the respective sections, those representative value, for example, their average, median, minimum, maximum or mode is computed or determined; and as illustrated in FIG. 3D, time series light intensity representative value data in which the representative values of light intensities or photon counts are aligned in time series is generated. In other words, the time series light intensity representative value data is time series data consisting of the representative values of light intensities or photon counts of the respective positions in the scanning track in the circulating movement of the light detection region along the scanning track. Then, when the time series light intensity representative value data is generated, the signal of a light-emitting particle is detected on the time series light intensity representative value data through processes of the fitting of a bell type function (FC), etc., in the manner described later; and the computation or determination of a characteristic of light of a light-emitting particle or a characteristic of a light-emitting particle itself using the signal of a light-emitting particle obtained from the time series light intensity representative value data will be conducted. In this regard, in the case of this manner, the effect of decreasing noise level relatively to the signal of a light-emitting particle is obtained. Generally, noises are generated irrespective of the position on a scanning track, but at random, while the signal of a light-emitting particle is always generated at the times corresponding to the almost same position on the scanning track, and therefore, in the step of determining the representative value of light intensities, the noise intensity is relatively reduced compared with the intensity of the signal of a light-emitting particle.

Figure 3E:
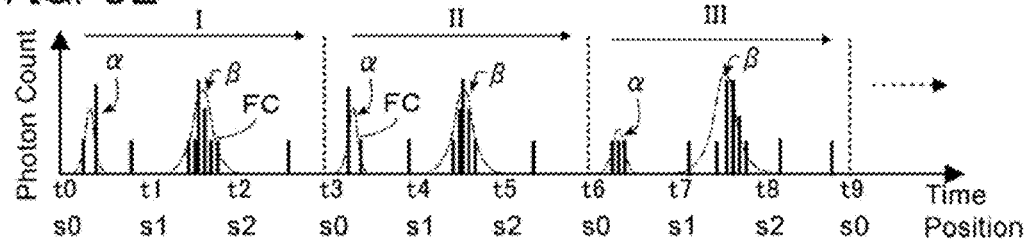

For the second manner, as illustrated in FIG. 3E, first, the detection of signals of light-emitting particles is performed in time series light intensity data obtained during the circulating movement of a light detection region along a scanning track. Then, as already noted, the signals of each light-emitting particle (in the drawing, α, β) on a scanning track almost periodically appear at the time corresponding to the same position on the scanning track, and thus, with reference to the signals of the respective light-emitting particles, computation of the representative value, for example, the average, median, minimum, maximum or mode, of the signals of each light-emitting particle is conducted, and by means of the representative values, computation or determination of a characteristic of light of a light-emitting particle or a characteristic of a light-emitting particle itself will be conducted.

Operation Processes of Scanning Molecule Counting Method

In the embodiment of the scanning molecule counting method in accordance with the present invention with the optical analysis device 1 as illustrated in FIG. 1A, concretely, there are conducted (1) a preparation of a sample solution containing light-emitting particles; (2) a process of measuring the light intensity of the sample solution and (3) a process of analyzing measured light intensities. FIG. 4 shows the processes in this embodiment in the form of flow chart. In this regard, FIG. 4A shows the processes in a case of detecting a signal of a light-emitting particle after the generation of time series light intensity representative value data; and FIG. 4B shows the processes in a case of determining the representative value of signals after detection of signals of a light-emitting particle. Further, FIG. 4C shows an example of the detection processing of the signal of a light-emitting particle.

(1) Preparation of a Sample Solution

The particle to be an observed object in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecules. When the particle to be an observed object is a particle which emits no light, there is used a particle to which a light emitting label (a fluorescence molecule, a phosphorescence molecule, and a chemiluminescent or bioluminescent molecule) is attached in an arbitrary manner. Typically, the sample solution is an aqueous solution, but not limited to this, and it may be an organic solvent or other arbitrary liquids.

(2) Measurement of Light Intensity of a Sample Solution (FIGS. 4A, 4B-Step 100)

The measurement of the light intensity in the optical analysis by the scanning molecule counting method of the present embodiment may be conducted in a manner similar to a measurement process of light intensity in FCS or FIDA except that the mirror deflector 17 and the stage position changing apparatus 17a are driven to move the position of the light detection region within the sample solution (scanning the sample solution) and move the sample solution during the measurement. In the operation processes, typically, after dispensing a sample solution into the well(s) 10 of the micro plate 9 and putting it on the stage of the microscope, when a user inputs to the computer 18 a command of starting a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 drives the mirror 7 (galvanomirror) to perform the circulating movement of the position of the light detection region along a scanning track in the well 10, and simultaneously with this, the photodetector 16 sequentially converts the detected light into electric signals and transmits them to the computer 18, which generates the time series light intensity data from the transmitted signals and stores it in an arbitrary manner. Then, after a predetermined number of times of the circulating movements of the position of the light detection region is completed, the stage position changing apparatus 17a moves the position of the micro plate 9 on the stage of a microscope, and again, the circulating movement of the position of the light detection region along the scanning track is performed while the generation and storing of time series light intensity data are conducted simultaneously. Then, these processes are repeated arbitrary times and one measurement is completed. In this regard, the photodetector 16 is typically a super high sensitive photodetector which can detect an arrival of a single photon, and thus when the detection of light is performed by the photon counting, the time series light intensity data may be time series photon count data.

The moving speed of the position of the light detection region in the circulating movement along a scanning track during the measurement of the light intensity may be a predetermined velocity set arbitrarily, for example, experimentally or in order to meet the purpose of an analysis. In a case of acquiring the information on the number density or concentration based on the number of detected light emitting particles, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

By the way, the moving speed of the position of the light detection region is preferably set to a value quicker than the moving speed in the random motion, i.e., the Brownian motion of a light-emitting particle in order to perform quantitatively precisely individual detection of a light-emitting particle to be observed from the measured time series light intensity data or the counting of the number of light-emitting particles, while satisfying the condition of the moving cycle time τ of the light detection region of the above-mentioned Expression (3). Since the particle to be observed in the inventive optical analysis technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 5A, whereby the light intensity changes at random (As noted, the excitation light intensity in the light detection region is reduced from the peak at the center of the region toward its outside.), so that it would become difficult to determine a significant light intensity change corresponding to each light-emitting particle. Then, preferably, as drawn in FIG. 5B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each light-emitting particle becomes almost uniform in the time series light intensity data as illustrated in the most upper row of FIG. 5C (When a light-emitting particle passes through the light detection region in an approximately straight line, the profile of the light intensity change forms a bell shape similar to the excitation light intensity distribution.) and the correspondence between each light-emitting particle and light intensity can be easily determined.

Concretely, the time Δt required for a light-emitting particle having a diffusion coefficient D to pass through the light detection region of radius Wo (confocal volume) by the Brownian motion is given from the equation of the relation of mean-square displacement:

$$(2Wo)^2 = 6D \cdot \Delta t \tag{5}$$

as:

$$\Delta t = (2Wo)^2 / 6D \tag{6},$$

and thus, the velocity of the light-emitting particle moving by the Brownian motion (diffusional moving velocity) Vdif, becomes approximately $$Vdif = 2Wo/\Delta t = 3D/Wo \quad (7)$$

Then, with reference to this, the moving speed of the position of the light detection region may be set to a value sufficiently quicker than Vdif. For example, when the diffusion coefficient of a particle to be observed is expected to be about $D=2.0\times10^{-10}$ m$^2$/s, Vdif will be $1.0\times10^{-3}$ m/s, supposing Wo is about 0.62 μm, and therefore, the moving speed of the position of the light detection region may be set to its 10 times or more, 15 mm/s, etc. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of the light intensity variation becomes an expected profile (typically, similar to the excitation light intensity distribution).

(3) Analysis of Light Intensity

When the time series light intensity data is obtained through the above-mentioned processes, by the processes in accordance with programs memorized in the storage apparatus in the computer 18, the detection of the signal of a light-emitting particle, the counting of light-emitting particles, various analyses, such as concentration calculation, are performed. Further, as already noted, especially in the present invention, the signal processing is conducted in either of the first manner of determining the representative values of light intensities in time series light intensity data before detection of the signal of a light-emitting particle and the second manner of determining the representative value of detected signals after detection of the signals of a light-emitting particle. In the followings, there are explained (i) the case that time series light intensity representative value data is generated before detection of the signal of a light-emitting particle (FIG. 4A) and (ii) the case that the representative value of detected signals is determined after detection of the signals of a light-emitting particle (FIG. 4B), respectively.

(i) The Case that Time Series Light Intensity Representative Value Data is Generated Before Detection of the Signal of a Light-emitting Particle (a) Process for Generation of Time Series Light Intensity Representative Value Data (FIG. 4A step 20)

In the process for generating time series light intensity representative value data, as described in the explanation with respect to FIG. 3C, time series light intensity data is divided into sections by the moving cycle τ of a light detection region, and with reference to the time tsi of the start point of each section (i is the number of the section), a light intensity value (a photon count) of each time [ti−i×tsi] (i is the number of the section) from the time tsi of the start point of each section is read out from data of the respective sections; and the representative value, i.e., the average, the median, the minimum, the maximum or the mode, of the read-out light intensities in the time [ti−i×tsi] of all the sections is computed or determined. Then, when the representative values of light intensities have been determined till the time tei of the end point of the sections, the time series light intensity representative value data, constructed by aligning in time series the representative values of the light intensities from the start time point is to the end time point te, is generated.

(b) Individual Detection of a Signal of a Light-Emitting Particle (See FIG. 4A Step 30 and FIG. 4C)

When the time series light intensity representative value data is generated by the above-mentioned process, on this light intensity data, the process of detecting the signal of a light-emitting particle individually is performed. As already noted, when the track of one light-emitting particle in its passing through the light detection region is approximately straight as shown in FIG. 5B, the light intensity variation on the light intensity data in the signal corresponding to the particle has a bell shaped profile reflecting the light intensity distribution in the light detection region determined by the optical system. Thus, basically in the scanning molecule counting method, when the time width Δτ of a signal for which width the light intensity value exceeding an appropriately set threshold value Ith continues is in a predetermined range, the signal having the profile of the light intensity may be judged to correspond to one particle having passed through the light detection region, and thereby one light-emitting particle is detected. And a signal whose light intensity does not exceed beyond the predetermined threshold Ith or whose time width Δτ is not within the predetermined range is judged as noise or a signal of a contaminant. Further, when the light intensity distribution in the light detection region can be assumed as a Gaussian distribution:

$$I = A \cdot \exp(-2t^2/a^2) \quad (8),$$

and when the intensity A and the width a, computed by fitting Expression (8) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

In an example of the process of the detection of a signal in light intensity, first, a smoothing treatment is performed to the light intensity data (FIG. 5C, the most upper row "detected result (unprocessed)") (FIG. 4C-step 110, FIG. 5C mid-upper row "smoothing"). Although the light emitted by a light-emitting particle is stochastic so that minute time gaps will be generated in data values, such gaps in the data values can be disregarded by the smoothing treatment. The smoothing treatment may be done, for example, by the moving average method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the light intensity data after the smoothing treatment, in order to detect a time domain (pulse existing region) in which a significant pulse form signal (referred to as "pulse signal" hereafter) exists, the first differentiation value with time of the smoothed light intensity data is computed (step 120). As illustrated in FIG. 5C, the mid-low row "time differential", in the time differential value of light intensity data, the value variation increases at the time of the signal value change, and thereby, the start point and the end point of a significant signal can be determined advantageously by referring to the time differential value.

Figure 6:
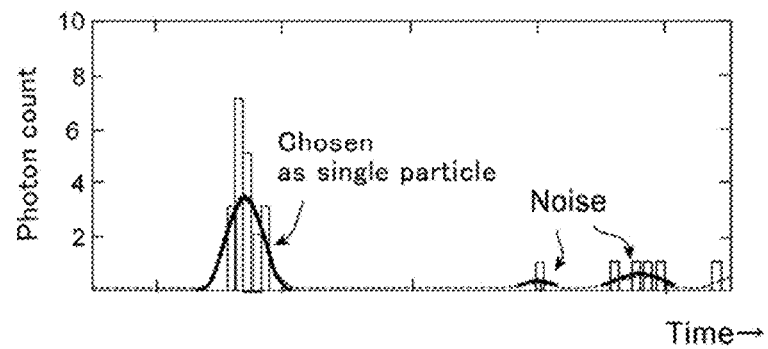
FIG. 6 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or contaminants.

After that, significant pulse signals are detected sequentially on the light intensity data (Steps 130-160). Concretely, first, on the time-differential value data of the light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed light intensity data in the pulse existing region (FIG. 5C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically Gauss function as in Expression (5), it may be Lorentz type function. Then, it is judged whether or not the computed parameters of the bell shaped function are within the respective ranges assumed for the parameters of the bell-shaped profile drawn by a pulse signal to be detected when one light-emitting particle passes through the light detection region, namely, whether or not the peak intensity, pulse width and correlation coefficient of a pulse are in the respective predetermined ranges (Step 150). Accordingly, the signal, whose computed parameters of the bell-shaped function are judged to be within the ranges assumed in a light signal corresponding to one light-emitting particle, as shown in FIG. 6 left, is judged as a signal corresponding to one light-emitting particle, and thereby one light-emitting particle has been detected. On the other hand, a pulse signal, whose computed parameters of the bell-shaped function are not within the assumed ranges, as shown in FIG. 6 right, is disregarded as noise. In this regard, simultaneously with detection of the signal of a light-emitting particle, the counting of the number of signals, i.e., the counting of light-emitting particle may be performed.

The searching and judging of a pulse signal in the above-mentioned processes of steps 130-150 may be repetitively carried out throughout light intensity data (step 160). In this connection, the processes for detecting individually a signal from the light intensity data may be performed by an arbitrary way, other than the above-mentioned procedures.

(ii) The Case that the Representative Value of Detected Signals is Determined after Detection of the Signals of Light-Emitting Particles As shown in FIG. 4B, in the case that the calculation or determination of the representative values of the detected light-emitting particle signals (step 30) after the detection processing (step 20) of the signal of a light-emitting particle is performed, first, the detection of the signals of light-emitting particles is performed in the time series light intensity data obtained in step 10, as it is, for example, in accordance with the fitting of the expression (8) or the processes shown in FIG. 4C, similarly to the above. In that time, the counting of the number of signals, i.e., the counting of light-emitting particles, may be performed simultaneously with the detection of the signals of light-emitting particles. Then, as schematically drawn in FIG. 3E, the time series light intensity data is divided into sections by the cycle period, and the intensity values (for example, peak intensities) of signals are picked up from the respective sections for each light-emitting particle; and those representative values, i.e., the averages, medians, minimums, maximums or mode is computed or determined.

(iii) Determination of Light-Emitting Particle Concentration

Further, in a case that the number of light-emitting particles is determined by counting the number of signals of detected light-emitting particles, when the volume of the whole region through which the light detection region has passed is computed out by an arbitrary way, the number density or concentration of the light-emitting particle in the sample solution can be determined from the number of light-emitting particles and the volume (Step 40).

The volume of the whole region through which the light detection region has passed may be theoretically computed out with the wavelength of excitation light or detected light, the numerical aperture of lenses and the adjustment condition of the optical system, but the volume may be determined experimentally, for instance, using the number of light-emitting particles detected by performing, with a solution having a known light-emitting particle concentration (a reference solution), the light intensity measurement, detection of (a) light-emitting particle(s) and their counting under the same condition as the measurement of a sample solution to be tested, and the light-emitting particle concentration of the reference solution. Concretely, for example, supposing the number of detected light-emitting particles is N in a reference solution of the light-emitting particle concentration C, the whole volume Vt of the region through which the light detection region has passed is given by:

$$Vt=N/C \qquad (9).$$

Alternatively, by preparing the plurality of solutions of different light-emitting particle concentrations and performing the measurement for each of the solutions, the average value of the computed Vts may be employed as the whole volume Vt of the region though which the light detection region has passed. Then, when Vt is given, the concentration c of the light-emitting particle of the sample solution, whose counting result of the light-emitting particles is n, is given by:

$$c=n/Vt \qquad (10)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage device of the computer 18 the information on the relations (Expression (9)) between concentrations C and light-emitting particle numbers N of various standard light-emitting particles for assumed moving patterns of the light detection region, so that a user of the device can appropriately use the memorized information on the relation in conducting an optical analysis.

(iv) Determination of Various Characteristics

When the detection of a light-emitting particle signal has been done, it becomes possible to acquire, using the signal intensity value, information (the feature quantity of a signal) related to various characteristics of the light of the light-emitting particle or the characteristics of the light-emitting particle itself, other than the light-emitting particle concentration. For instance, in the measurement of detected light, in which a detected light is measured in each polarization direction independently and light intensity data are generated for each of the polarization directions, an arbitrary index value indicating polarization characteristics, such as a polarization degree and polarization anisotropy, can be computed from the intensity values of signals acquired from those respective light intensity data so that, from such an index value, an index value of the rotatory diffusion characteristics of the light-emitting particle can be computed. Furthermore, in the measurement of detected light, in which components of a plurality of wavelength bands in a detected light are separately measured and light intensity data are generated for each of the wavelength bands, it becomes possible to acquire information (e.g., intensity ratio in two or more wavelengths) on the emission wavelength spectrum of a light-emitting particle from the intensity values of the signals acquired from those light intensity data. Here, it should be understood that, in the scanning molecule counting method that the present invention is directed to, the information on the characteristics of light of a light-emitting particle, the characteristics of light-emitting particle itself as above can be determined for each light-emitting particle. Moreover, in the present invention, since the light intensity values in multiple times measurements are obtained per light-emitting particle and those representative values are determined, the reduction of the scattering and the improvement of the detection accuracy in the information on characteristics of the light of light-emitting particles or characteristics of the light-emitting particles (in comparison with a case of performing a measurement only once per light-emitting particle) are expected.

Thus, according to the above-mentioned the present invention, in the scanning molecule counting method, through making the light detection region pass through a predetermined route and repetitively measuring the light emitted by the same light-emitting particle multiple times during the period of making the light detection region pass through a predetermined route, the suppression of the scattering and the improvement of the detection accuracy in the detection of the existence of each light-emitting particle and/or its characteristic with the measured light intensity data will be achieved In order to verify the validity of the present invention explained above, the experiments described below were conducted. In this regard, it should be understood that the following embodiments illustrate the validity of the present invention only, not intended to limit the scope of the present invention.

Embodiment 1

In accordance with the above-mentioned scanning molecule counting method, signals of light-emitting particles were detected from time series light intensity data obtained by the light measurement during the circulating movement of a light detection region along a predetermined route, and the relation between the scatterings of the peak intensities of the light-emitting particle signals and the numbers of circulations of the light detection region was evaluated.

For the sample solution, there was prepared a solution containing 10 nM fluorescent dye SYTOX Orange (Invitrogen Corp., Cat. No. S-11368) and 1 pM Plasmid pbr322 (Takara Bio, Inc., Cat. No. 3035) in phosphate buffer (containing 0.05% Tween 20). SYTOX Orange is a DNA intercalater dye, whose fluorescence intensity increases about 500 times when it binds with a DNA. In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) was acquired for the above-mentioned sample solution in accordance with the manner explained in the above-mentioned "(2) Measurement of Light Intensity of a Sample Solution". In that time, a 633-nm laser light was used for excitation light, and, using a band pass filter, the light of the wavelength bands, 660 to 710 nm, was measured. The scanning track of the position of the light detection region in the sample solution was a circle of about 24 μm in radius; the moving speed was 15 mm/sec.; the cycle time of the circulating movement was 10 m seconds (=6000 rpm); BIN TIME was set to 10 μseconds and the light measurement for 2 seconds was performed.

In data processing after the light measurement, in accordance with the manner of generating time series light intensity representative value data before detecting signals of light-emitting particles explained with respect to FIG. 3C, the time series light intensity data was divided into sections of the moving cycle time: 10 msec.; and the average value of photon count values was computed for each time from the start point of each section (by BIN TIME) so that the representative value data of the time series photon count values was generated. Then, in the representative value data, individual detection of signals of light-emitting particles was performed. In the detection of signals of light-emitting particles, in accordance with the manner, described in "(b) Individual detection of the signal of a light-emitting particle" and steps 110-160 of FIG. 4C, the smoothing treatment was applied to the time series photon count representative value data, and after determining the start point and end point of each pulse signal in the smoothed data, the fitting of a Gauss function to each pulse signal was carried out by the least-squares method, and thereby, the peak intensity, pulse width (full width at half maximum) and correlation coefficient (in the Gauss function) were determined. Then only a pulse signal satisfying the following conditions:

20 μseconds<pulse width <400 μseconds

Peak intensity >1[pc/10 μsec.]

Correlation coefficient >0.95,　　(A)

was extracted as a signal corresponding to a light-emitting particle, and the average value and CV value of the peak intensities of the extracted light-emitting particle signals (the peak intensity is one of the characteristic values of a signal.) were computed.

Figure 7:
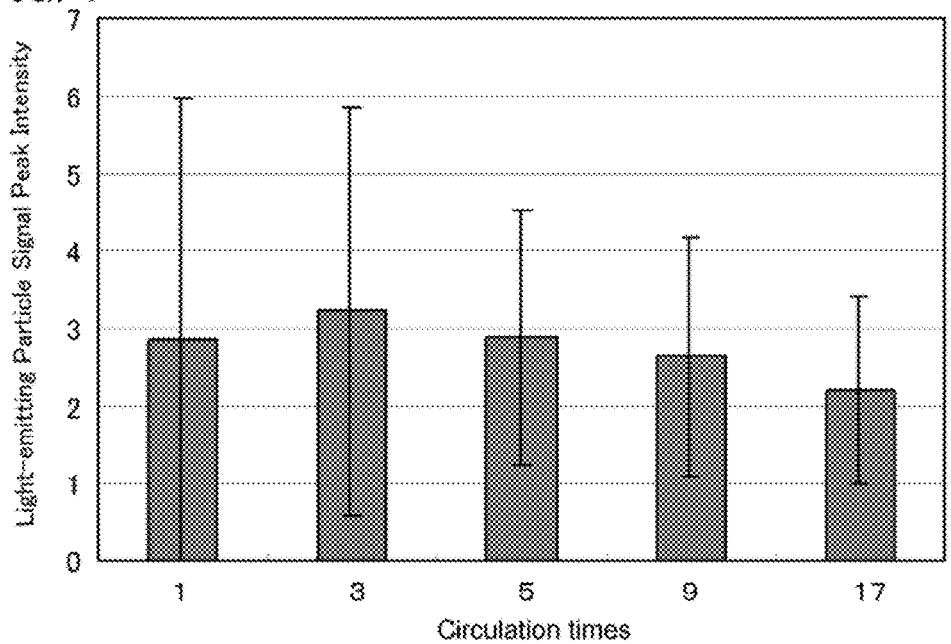
FIG. 7 shows changes, to the number of circulations along a scanning track of a light detection region, of average values (bar graph) and CV values (error bar) of the peak intensities of light-emitting particle signals obtained by the scanning molecule counting method performed in accordance with the present invention using a fluorescently labeled plasmid as a light-emitting particle.

FIG. 7 shows the variations of the average value and CV value of the peak intensities of the detected light-emitting particle signals (in the time series photon count representative value data) when the numbers of data sections, i.e. the number of circulations of the light detection region in one scanning track was changed in generating time series photon count representative value data (time series average value data). As understood from the drawing, although no very big changes of the average value of the peak intensities were seen in 1-9 circulations, the CV value, an index value of scattering in the values, was reduced with the increase of the number of circulations. Especially, while the CV value in the case of one circulation was 110%, the CV value in the case that the number of circulations was 17 times was reduced to 55%, and thus, the scattering in the values was suppressed. [The reason of the reducing of the average value of peak intensities with the increase of the number of circulations is considered to be because the position of a light-emitting particle moves gradually so that the photon count value disperses to the previous or later time.] This result shows that according to the way of the present invention, the scattering in characteristic values of light-emitting particle signals can be reduced, and the detection accuracy can be improved.

Embodiment 2

Figure 8:
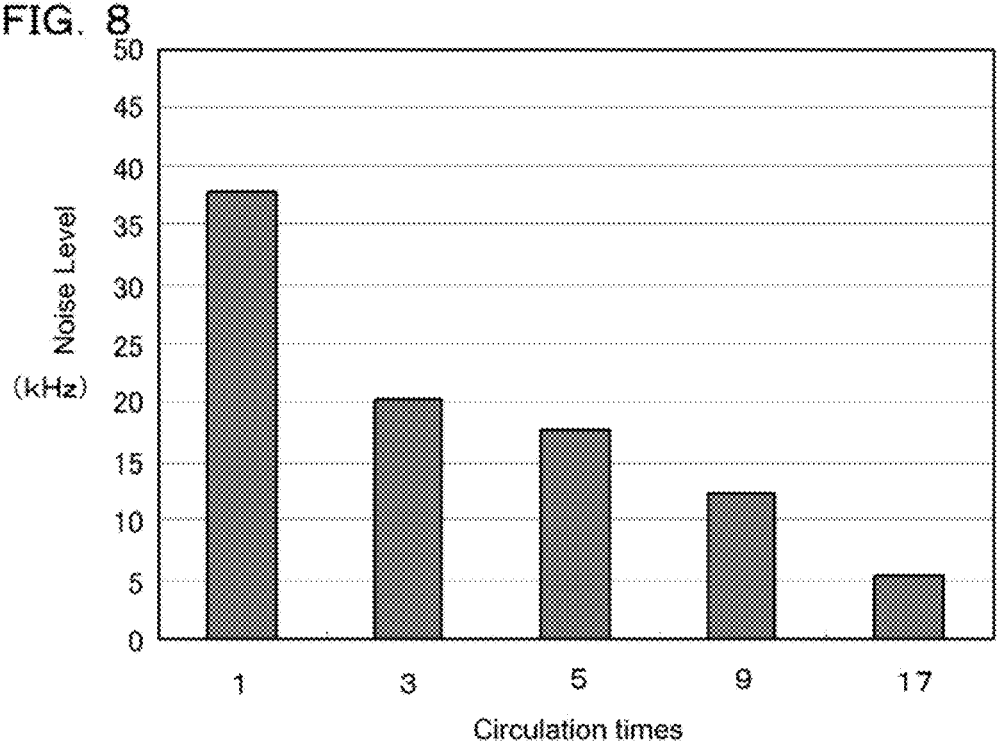
FIG. 8 shows changes of noise amounts on time series light intensity data to the number of circulations of a light detection region along a scanning track in the scanning molecule counting method performed according to the present invention.

After performing the light detection and the preparation of time series photon count representative value data in the same manner as in Embodiment 1 using the phosphate buffer (containing no light-emitting particles) of Embodiment 1 as a sample solution, reference values (noise level) obtained by adding three times value of the standard deviation to the average value of the photon counts of the representative value data in the whole region were computed as an index value of the magnitude of background noise. FIG. 8 shows variation of the above-mentioned noise level when the number of sections of the data in generating time series photon count representative value data, namely, the number of circulations of the light detection region in one scanning track was changed. As understood from the drawing, the noise level was reduced as the number of circulations increased. As noted, background noise is generated at random irrespective of the positions of the light detection region in the scanning track. That is, the possibility that background noise is repeatedly generated at the time corresponding to the same position in the scanning track is extremely low, and thus, it is considered that, as the number of sections, referred to in generating time series photon count representative value data, is larger, the intensity of background noise decreases relatively to the intensity of the signal of a light-emitting particle generated at the times corresponding to the almost same position in the scanning track. This was confirmed with the result of FIG. 8.

Embodiment 3

In an optical analysis device, a polarizer was inserted in the excitation light optical path, polarizing the excitation light in one direction, and the component $I_V$ in the direction perpendicular to the polarization direction of excitation light and the component $I_H$ in the direction parallel to the polarization direction of excitation light were detected, respectively, by inserting a polarization beam splitter in the detected light optical path; and then, signals of light-emitting particles were detected by performing the light measurement and data processing under the same conditions as in Embodiment 1 except the above-mentioned conditions. And, using the obtained light-emitting particle signals, the polarization degree $(I_V-I_H)/(I_V+I_H)$ was computed for each light-emitting particle, and their average value and CV value were computed.

Figure 9:
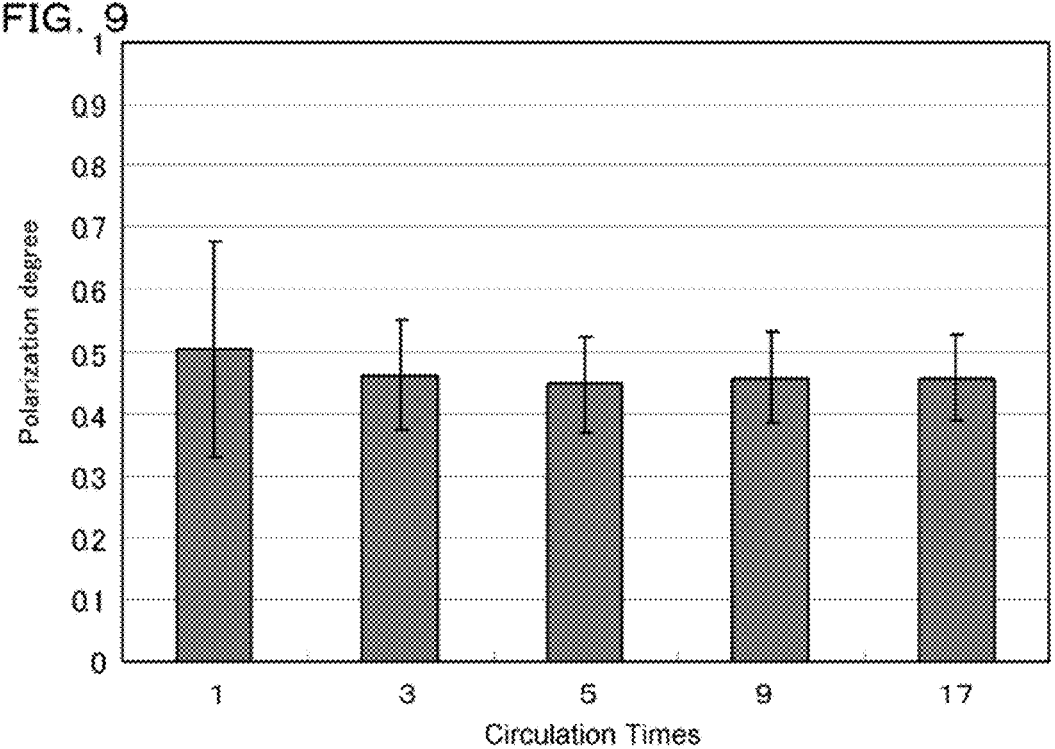
FIG. 9 shows changes, to the number of circulations of a light detection region along a scanning track, of average values (bar graph) and a standard deviation (error bar) of polarization degrees of light-emitting particles obtained by the scanning molecule counting method performed according to this invention.

FIG. 9 shows variations of the average value and CV value of the polarization degrees of light-emitting particle signals when the number of sections of the data in generating time series photon count representative value data, namely, the number of circulations of the light detection region in one scanning track was changed. As understood from the drawing, although no very big changes of the average values of the polarization degree itself were seen in 1-17 circulations, the CV value, an index value of scattering in the values, was reduced when the number of circulations increased. Especially, while the CV value in the case of one circulation was 35%, the CV value in the case that the number of circulations was 17 times was reduced to 16%, and thus, the scattering in the values was suppressed. These results show that, according to the way of the present invention, the scattering in characteristic values of light-emitting particle signals can be reduced and the detection accuracy can be improved.

Embodiment 4

Detection of the signals of light-emitting particles is performed by the scanning molecule counting method according to the present invention, using fluorescent dye solutions of various concentrations as sample solutions, and the lower limit of the light-emitting particle concentration which can be determined by the scanning molecule counting method in accordance with the present invention was checked.

For sample solutions, there were prepared solutions containing 1 aM~10 nM fluorescent dye ATTO647N (Sigma-Aldrich) in phosphate buffer (containing 0.05% Tween 20). In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) were acquired for the above-mentioned dye solutions containing fluorescent dyes and a buffer solution containing no fluorescent dye in accordance with the manner explained in the above-mentioned "(2) Measurement of Light Intensity of a Sample Solution". In that time, a 633-nm laser light was used for excitation light, and, using a band pass filter, the light of the wavelength bands, 660 to 700 nm, was measured, and time series photon count data were generated. The scanning track of the position of the light detection region in the sample solution was a circle of about 72 μm in radius; the moving speed was 90 mm/sec.; the cycle time of the circulating movement was 5 m seconds (=12000 rpm); BIN TIME was set to 10 μseconds and the light measurement for 600 seconds was performed.

In the data processing after the light measurement, in accordance with the manner of generating time series light intensity representative value data before detection of signals of light-emitting particles, as explained in relation to FIG. 3C, the time series light intensity data was divided into sections by the moving cycle: 5 m seconds; the average value of the photon count values of the data of three circulations was computed for each time (for each BIN TIME) from the start points of each classification; and thereby, the representative value data of the time series photon count values was generated. And in the representative value data, individual detection of signals of light-emitting particles was performed as in the case of Embodiment 1, and the number of the detected light-emitting particle signals was counted.

FIG. 10 shows the detected numbers (axis of ordinate) of the light-emitting particle signals in the cases of using the dye solutions of the respective concentrations (axis of abscissa). In the drawing, the numbers of particles detected in the average value data of the data of three circulations in three times of the measurements for 600 seconds (with superposing process •) and the numbers of particles detected in the data of one circulation (without superposing process Δ) are plotted, respectively. With reference to the drawing, while the linearity between the numbers of detected particles and dye concentrations was lost in 1 fM or less in the case without superposing process, the linearity between the numbers of detected particles and dye concentrations was obtained to 100 aM in the case with superposing process. This fact shows that, according to this invention, the discrimination between a light-emitting particle signal and a noise signal becomes easier and the measuring sensitivity is improved.

Thus, as understood from the above-mentioned results of the embodiments, when light from one light-emitting particle is measured multiple times by circulating the light detection region along the same predetermined route in accordance with the teachings of the present invention, the scattering in characteristic values of light-emitting particle signals is reduced, and thereby, the detection accuracy is improved. Furthermore, in a case of generating time series light intensity representative value data, background noise decreases relatively and the improvement of the S/N ratio is expected.

The invention claimed is:

1. An optical analysis device which detects light from a light-emitting particle dispersed and moving at random in a sample solution using an optical system of a confocal microscope or a multiphoton microscope, comprising:
   a light detection region circulator which circulates a position of a light detection region of the optical system along a predetermined route in the sample solution by moving an optical path of the optical system, the light detection region circulator being electronically controlled;
   a computer programmed to control the circulator of the light detection region circulator;
   a light detector which detects light from the light detection region; and
   a signal processor which generates time series light intensity data of the light from the light detection region detected with the light detector during each circulation of the position of the light detection region in the sample solution and detects a signal indicating light from each light-emitting particle individually in the time series light intensity data;
   wherein the light detection region circulator circulates the position of the light detection region along the predetermined route, and the signal processor uses the time series light intensity data obtained during the circulation of the position of the light detection region along the predetermined route for the at least two times to detect a signal indicating light from each light-emitting particle individually, based on a representative value, the representative value being determined based on light intensity values of the light from each light-emitting particles detected two or more times,
   wherein the position of the light detection region is circulated along the predetermined route with a cycle time which is shorter than a diffusion time until the light-emitting particle deviates by diffusion from the predetermined route of the light detection region, and
   wherein the circulation of the position of the light detection region and the detection of light from the light detection region are performed two or more times before the signal is detected individually with the signal processor.

2. The device of claim 1,
   wherein the position of the sample solution is moved to a new position after the circulating of the position of the light detection region along the predetermined route of a predetermined number of circulations,
   wherein, after the sample solution is moved to the new position, the position of the light detection region of the optical system in the sample solution is circulated along the predetermined route at least two times by changing the optical path of the optical system with the light detection region circulator,
   wherein, at the new position, the light is detected from the light detection region with the light detection portion,
   wherein, at the new position, time series light intensity data is generated with the signal processor, and
   wherein, for each position after moving the sample solution, individual detection of the signals indicating light from the respective light-emitting particles existing in the predetermined route in time series light intensity data is conducted.

3. The device of claim 1, wherein the signal processor generates time series light intensity representative value data consisting of representative values of the light intensity values determined for the respective positions in the predetermined route in the time series light intensity data, and detects a signal indicating light from each light-emitting particle individually in the time series light intensity representative value data, and detects a characteristic value of the signal.

4. The device of claim 1, wherein the signal processor detects signals indicating light from each light-emitting particle individually in the time series light intensity data; detects characteristic values of each of the signals; and computes a representative value of the characteristic values of the signals for each light-emitting particle.

5. The device of claim 3, wherein the characteristic value of the signal is at least one selected from a group of a light intensity, a photon count, a polarization degree, a rotational diffusion constant and an emission spectrum.

6. The device of claim 1, wherein the signal processor counts a number of individually detected signals indicating light from the light-emitting particles to count a number of the light-emitting particles detected during the circulating of the position of the light detection region.

7. The device of claim 1, wherein the signal processor detects that one light-emitting particle has entered into the light detection region when a signal indicating light having a larger intensity than a predetermined threshold value is detected.

8. The device of claim 1, wherein the signal processor smoothes the time series light intensity data; and detects a bell-shaped pulse form signal having an intensity exceeding beyond a predetermined threshold value as a signal indicating light from a single light-emitting particle in the smoothed time series light intensity data.

9. An optical analysis method of detecting light from a light-emitting particle dispersed and moving at random in a sample solution using an optical system of a confocal microscope or a multiphoton microscope, comprising steps of:
   (a) circulating a position of a light detection region of the optical system along a predetermined route with a cycle time which is shorter than a diffusion time until the light-emitting particle deviates by diffusion from the predetermined route of the light detection region, by moving an optical path of the optical system with a light detection region circulator controlled electronically;
   (b) detecting light from the light detection region with a light detector and generating time series light intensity data with a signal processor during each circulation of the position of the light detection region; and
   (c) detecting individually a signal indicating light from each light-emitting particle existing in the predetermined route with the signal processor based on a representative value, the representative value being determined based on light intensity values of the light from each light-emitting particles detected two or more times,
   wherein steps (a) and (b) are repeated two or more times before step (c) and
   wherein step (a) is controlled by a computer programmed to control the circulation of the light detection region.

10. The method of claim 9, further comprising steps of:
   (d) moving the position of the sample solution to a new position after completing steps (a) and (b);
   (e) repeating steps (a) and (b) at the new position; and performing the step (c) for each position after moving the sample solution.

11. The method of claim 9, further comprising a step of:
(f) generating time series light intensity representative value data consisting of representative values of the light intensity values determined for the respective positions in the predetermined route in the time series light intensity data which were obtained in steps (a) and (b),
wherein, in the step (c), a signal indicating light from each light-emitting particle individually is detected in the time series light intensity representative value data and a characteristic value of the signal is detected.

12. The method of claim 9, further comprising steps of:
(g) detecting signals indicating light from each light-emitting particle individually in the time series light intensity data from the time series light intensity data which were obtained in steps (a) and (b);
(h) detecting characteristic values of each of the signals; and
(i) computing a representative value of the characteristic values of the signals for each light-emitting particle in the step (c).

13. The method of claim 11, wherein the characteristic value of the signal is at least one selected from a group of a light intensity, a photon count, a polarization degree, a rotational diffusion constant and an emission spectrum.

14. The method of claim 9, further comprising a step of (j) counting a number of individually detected signals indicating light from the light-emitting particles to count a number of the light-emitting particles detected during the circulating of the position of the light detection region.

15. The method of claim 9, wherein, in the step (c), it is detected that one light-emitting particle has entered into the light detection region when a signal indicating light having a larger intensity than a predetermined threshold value is detected.

16. The method of claim 9, wherein, in the step (c), the time series light intensity data is smoothed; and a bell-shaped pulse form signal having an intensity exceeding beyond a predetermined threshold value is detected as a signal indicating light from a single light-emitting particle in the smoothed time series light intensity data.

17. The method of claim 9, further comprising a step of (k) determining a concentration of the light-emitting particle in the sample solution based on a number of the detected light-emitting particles.

18. A computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising:
(a) circulating a position of a light detection region of the optical system along a predetermined route with a cycle time which is shorter than a diffusion time until the light-emitting particle deviates by diffusion from the predetermined route of the light detection region, by moving the optical path of the optical system with a light detection region circulator controlled electronically;
(b) detecting light from the light detection region with a light detector and generating time series light intensity data with a signal processor during each circulation of the position of the light detection region; and
(c) detecting individually a signal indicating light from each light-emitting particle existing in the predetermined route with the signal processor based on a representative value, the representative value being determined based on light intensity values of the light from each light-emitting particles detected two or more times,
wherein steps (a) and (b) are repeated two or more times before step (c) and
wherein step (a) is controlled by the computer programmed to control the circulation of the light detection region.

* * * * *